US006787318B1

(12) United States Patent
Tan et al.

(10) Patent No.: US 6,787,318 B1
(45) Date of Patent: Sep. 7, 2004

(54) ASSAY FOR EVALUATING THE THERAPEUTIC EFFECTIVENESS OF AGENTS IN REDUCING ALZHEIMER'S DISEASE PATHOLOGY

(75) Inventors: Jun Tan, Tampa, FL (US); Terrence Town, Tampa, FL (US); Michael Mullan, Tampa, FL (US)

(73) Assignee: Roskamp Research Institute, LLC, Bradenton, FL (US)

( * ) Notice: Subject to any disclaimer, the term of this patent is extended or adjusted under 35 U.S.C. 154(b) by 0 days.

(21) Appl. No.: 09/585,058

(22) Filed: Jun. 1, 2000

Related U.S. Application Data

(60) Provisional application No. 60/137,016, filed on Jun. 1, 1999.

(51) Int. Cl.[7] .......................... G01N 33/53; G01N 33/567

(52) U.S. Cl. .......................... 435/7.1; 435/7.2; 435/7.8; 435/975

(58) Field of Search .......................... 435/7.8, 7.1, 7.2, 435/975

(56) References Cited

U.S. PATENT DOCUMENTS 3,791,932 A 2/1974 Schurrs et al.
3,839,153 A 10/1974 Schurrs et al.
3,850,578 A 11/1974 McOnnell
3,850,752 A 11/1974 Schurrs et al.
3,853,987 A 12/1974 Dreger
3,867,517 A 2/1975 Ling
3,879,262 A 4/1975 Schurrs et al.
3,901,654 A 8/1975 Gross
3,935,074 A 1/1976 Rubenstein et al.
3,984,533 A 10/1976 Uzgiris
3,996,345 A 12/1976 Ullman et al.
4,034,074 A 7/1977 Miles
4,098,876 A 7/1978 Piasio et al.
4,439,196 A 3/1984 Higuchi
4,447,224 A 5/1984 DeCant et al.
4,447,233 A 5/1984 Mayfield
4,475,196 A 10/1984 La Zor
4,486,194 A 12/1984 Ferrara
4,487,603 A 12/1984 Harris
4,666,828 A 5/1987 Gusella
4,683,202 A 7/1987 Mullis
4,736,866 A 4/1988 Leder et al.
4,801,531 A 1/1989 Frossard
4,866,042 A 9/1989 Neuwelt
4,879,219 A 11/1989 Wands et al.
4,925,678 A 5/1990 Ranney
4,959,217 A 9/1990 Sanders et al.
5,011,771 A 4/1991 Bellet et al.
5,167,616 A 12/1992 Haak et al.
5,169,383 A 12/1992 Gyory et al.
5,175,383 A 12/1992 Leder et al.
5,175,384 A 12/1992 Krimpenfort et al.
5,175,385 A 12/1992 Wagner et al.
5,192,659 A 3/1993 Simons
5,221,778 A 6/1993 Byrne et al.
5,225,182 A 7/1993 Sharma
5,272,057 A 12/1993 Smulson et al.
5,281,521 A 1/1994 Trojanowski et al.
5,288,846 A 2/1994 Quertermous et al.
5,298,422 A 3/1994 Schwartz et al.
5,347,075 A 9/1994 Sorge
5,360,735 A 11/1994 Weinshank et al.
5,387,742 A 2/1995 Cordell et al.
5,434,050 A * 7/1995 Maggio et al.
5,464,764 A 11/1995 Capecchi et al.
5,487,992 A 1/1996 Capecchi et al.

FOREIGN PATENT DOCUMENTS

WO 9314200 7/1993
WO 9406908 3/1994
WO 9423049 10/1994
WO 9428123 12/1994

OTHER PUBLICATIONS

Nguyen et al., *Eur. J. Immunol.*, vol. 28, pp. 2537–2548, 1998.*

Gerriste et al., *PNAS, U.S.A.*, vol. 93, pp. 2499–2504, 1996.*

Suo et al., Alzheimer's Beta–amyloid peptides induce inflammatory cascade in human vascular cells: the roles of cytokines and CD40, Jul. 28, 1998, Brain Research, 807, pp. 110–117.*

Wu et al., Drug Targeting of a peptide radiopharmaceutical through the primate blood–brain barrier in vivo with a monoclonal antibody to the human insulin receptor. Oct. 1997, J. Clinical Investigation, vol. 100, No. 7, pp. 1804–1812.*

Ausubel et al., *Current Protocols in MOlecular BIology*, John WIley and Sons, Baltimore, Maryland (1989).

Birren et al (eds) *Genome Analysis: A Laboratory Manual Series*, Vols. 1–4 Cold Spring Harbor Laboratory Press, New York (1998).

Borreback, *Antibody Engineering—A Practical Guide*, W.H. Freeman and Co., 1992.

Burke and Olson (1991).

Capecchi (1989).

Castillo, G.M., Ngo, C., Cummings, J., Wight, T.N. and Snow, A.D., *J. Neurochem* 69, 2452 (1997).

(List continued on next page.)

*Primary Examiner*—Gary Kunz
*Assistant Examiner*—Stephen Gucker
(74) *Attorney, Agent, or Firm*—Webb Ziesenheim Logsdon Orkin & Hanson, P.C.

(57) ABSTRACT

There is provided an assay method for determining the effect of an agent on Alzheimer's Disease pathology by treating microglial cells with Aβ peptides, adding CD40 ligand to the microglial cells, adding a therapeutic agent to the microglial cells, and measuring Alzheimer's Disease pathology. Also provided is a method of determining therapeutic effectiveness of an agent for Alzheimer's Disease by measuring the inhibition of CD40–CD40L binding in the presence of the agent. An assay for determining the effect of an agent on Alzheimer's Disease pathology having Aβ peptides for adding to microglial cells, CD40 ligand for being added to the microglial cells, a therapeutic agent being added to the microglial cells and a measuring device for reassuring Alzheimer's Disease pathology is also provided.

12 Claims, 12 Drawing Sheets

OTHER PUBLICATIONS

Chang et al., *Somatic Gene Therapy*, CRC Press, Ann Arbor, MI (1995).
Combs, C.K., Johnson, D.E., Cannady, S.B., Lehman T.M and Landreth, G.E., *J. Neurosci.* 19, 928 (1999); R. N. Kalaria, *Curr. Opin. Hematol.* 6, 15 (1999).
Culver, 1998.
Davies et al. (1992).
Denfeld, R.W., et al., *Eur. J. Immunol.* 26, 2329 (1996).
Dickinson et al. (1993).
Duff and Lincoln (1995).
Ellis, R. J. et al., *Neurology* 46, 1592 (1996).
"Gene Therapy" (Advances in Pharmacology 40, Academic Press, 1997).
Genis, I., Fisher, A., Michaelson, D.M., *J. Neurochem.* 72, 206 (1999).
Gilboa et al (1986).
Harlow and Lane, *Antibodies: A Laboratory Manual*, Cold Spring Harbor Laboratory, Cold Spring Harbor, NY, 1988.
Henn, V. et al., *Nature* 391, 591 (1998).
Higgins, L.S., Rodems, J.M., Catalano, R., Quon D., and Cordell, B., *Proc. Natl. Acad. Sci. USA* 92, 4402 (1995).
Hollenbaug, D., et al., *J. Exp. Med.* 182, 33 (1995).
Hsiao, K.K., et al., Neuron 15, 1203 (1995).
Hsiao, K.K., et al., Science 274, 99 (1996).
Huberman, M. et al., *J. Neuroimmunol.* 52, 147 (1994).
Huxley et al. (1991).
Jakobovits et al. (1993).
James, N.D., et al., *Neurobiol. Aging* 17, 235 (1996).
Johnson and Bird, 1991.
Johnstone & Thorpe, *Immunochemistry in Practice*, Blackwell Scientific Publications, Oxford, 1982.
Lamb et al. (1993).
Huston et al, 1991.
Kalaria, 1999.
Karmann, K., Hughes, C.C., Schechner, J., Fanslow, W.C. and Pober, J.S. *Proc. Natl. Acad. Sci. USA* 92, 4342 (1995).
Klegeris, A., Walker, D.G. and P. L. McGeer, *Brain Res.* 747, 114 (1997).
Li, Q.X. et al., *Blood* 84, 133 (1994).
Mach, F., et al., *Proc. Natl. Acad. Sci. USA* 94, 1931 (1997).
Marshak et al, "Strategies for Protein Purification and Characterization. A laboratory course manual." CSHL Press, 1996.
Meda. L. et al., *Nature* 374, 647 (1995).
Meda et. al., 1999.
Mernaugh and Mernaugh, 1995.
Mishell and Shiigi (eds), Selected Methods in Cellular Immunology, W.H. Freeman and Co., New York (1980).
Oleana, V.H., Salehi, A. and Swaab, D.F., *Neuroreport* 9, 1451 (1998).
Pearson and Choi (1993).
Perbal, *A Practical Guide to Molecular Cloning*, John Wiley & Sons, New York (1988).
*PCR Protocols: A Guide To Methods And Applications*, Academic Press, San Diego, CA (1990).
Rogers, J., Luber–Narod, J., Styren, S.D. and Civin, W.H., *Neurobiol. Aging* 9, 339 (1988).
Rothstein (1991).
Ruggiero, G., et al., *J. Immunol.* 156, 3737 (1996).
Sambrook et al., *Molecular Cloning: A Laboratory Manual*, Cold Spring Harbor Laboratory Press, New York (1989).
Schedl et al. (1993).
Schneider, A., Biernat, J., von Bergen, M., Mandelkow, E., and Mandelkoq, E.M., *Biochemistry* 38, 3549 (1999).
Schonbeck, U. et al., *J. Biol. Chem.* 272, 19569 (1997).
Sempowski, G.D., Chess, P.R. and Phipps, R.P., *J. Immunol.* 158, 4670 (1997).
Stites et al.(eds), Basic and Clinical Immunology (8th Edition), Appleton & Lange, Norwalk, CT (1994).
Strauss et al. (1993).
Sturchler–Pierrat, C., et al., *Proc. Natl. Acad. Sci. USA* 94, 13287 (1997).
Tan, J., et al., J. Neuroimmunol. 97, 77 (1999).
Testoni et al, 1996, Blood 87:3822.
Uchihara, T., Akiyama, H., Kondo, H. and Ikeda, K., *Stroke* 28, 194 (1997).
*Vectors: A Survey of Molecular Cloning Vectors and Their Uses*, Butterworths, Boston MA (1988).
Vega et al., *Gene Targeting*, CRC Press, Ann Arbor, MI (1995).
Watson et al., *Recombinant DNA*, Scientific American Books, New York.
Xu, J., et al., *Immunity* 1, 423 (1994).

* cited by examiner

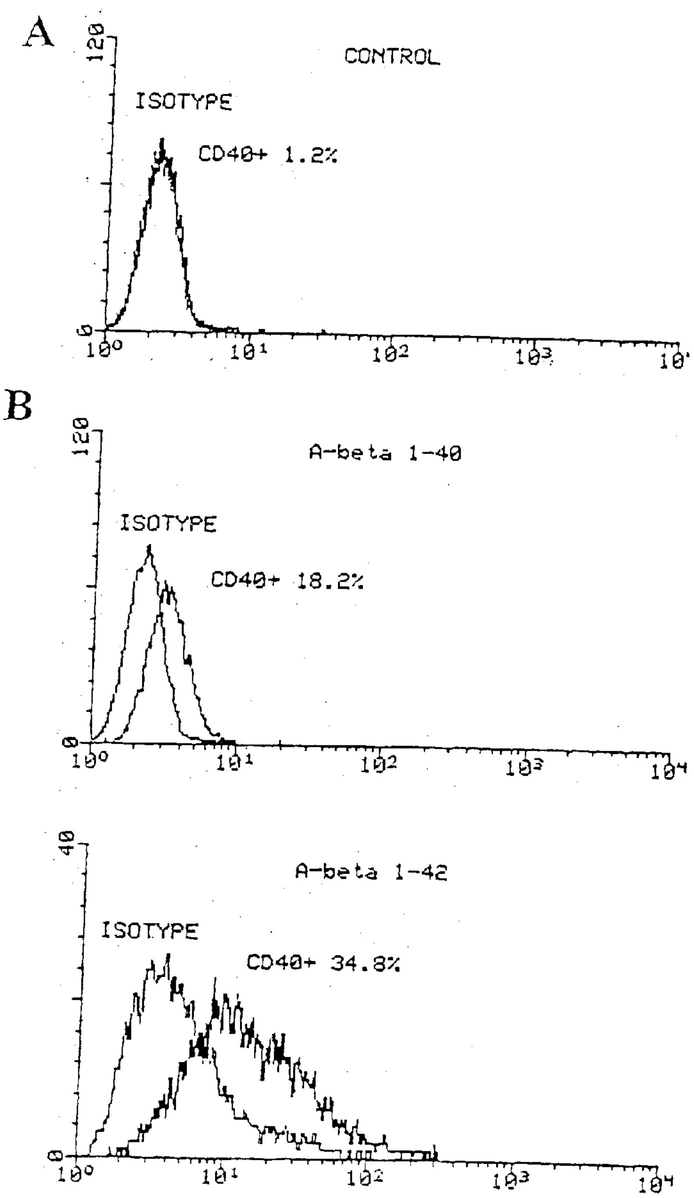
Figs. 1A-C

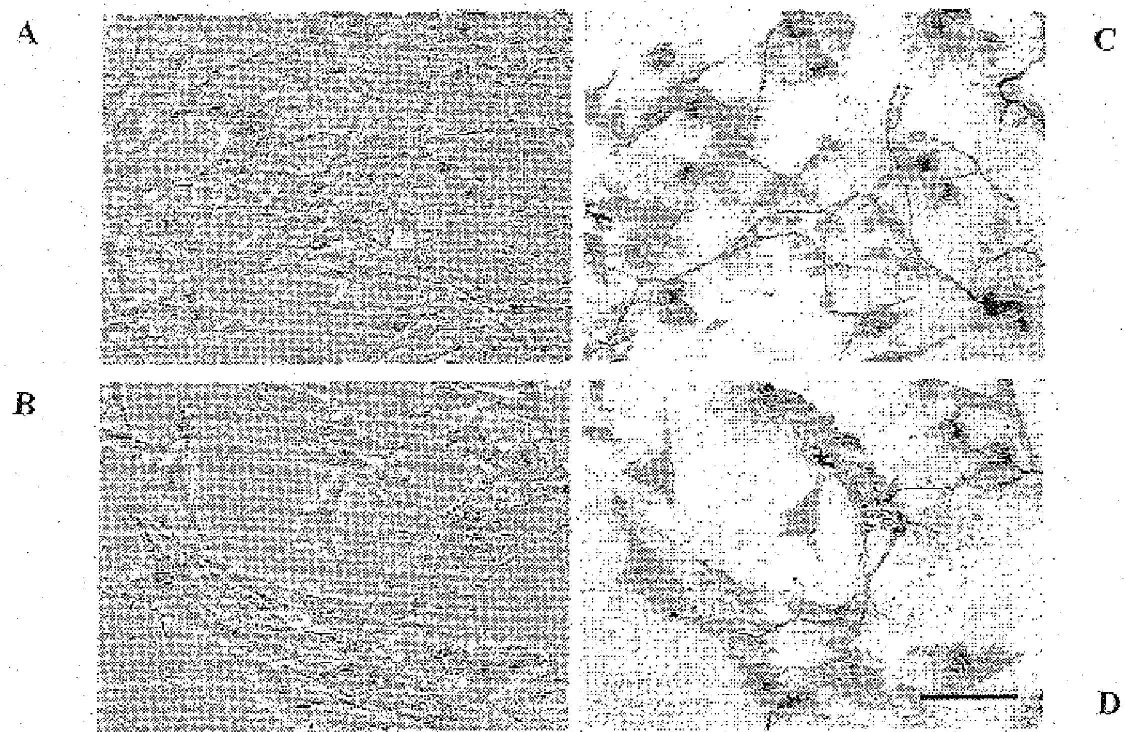
Figs. 2A-D

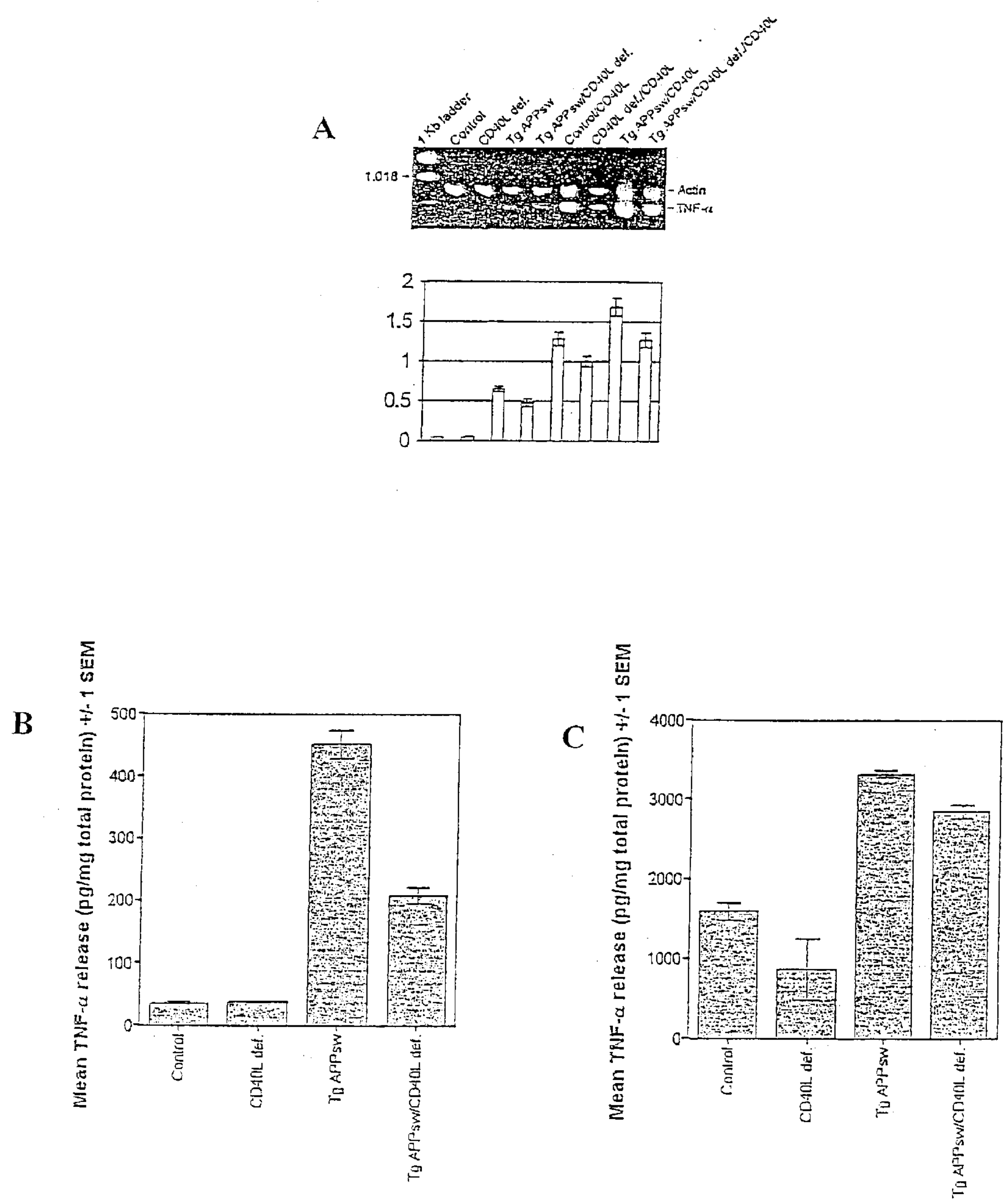
Figs. 3A-C

Figs. 5A-E

A
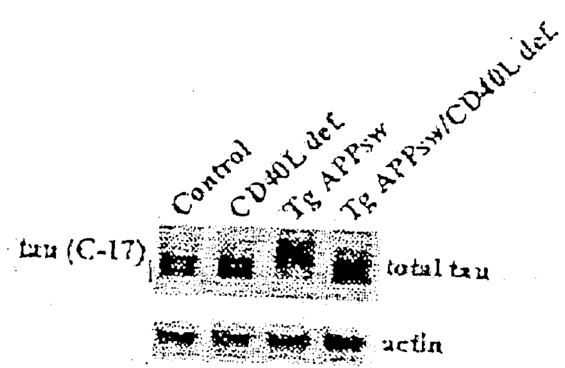
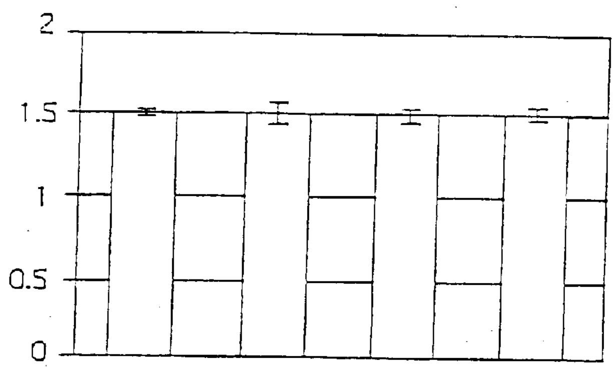
B
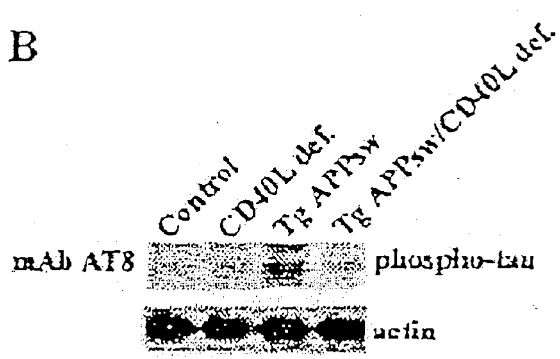
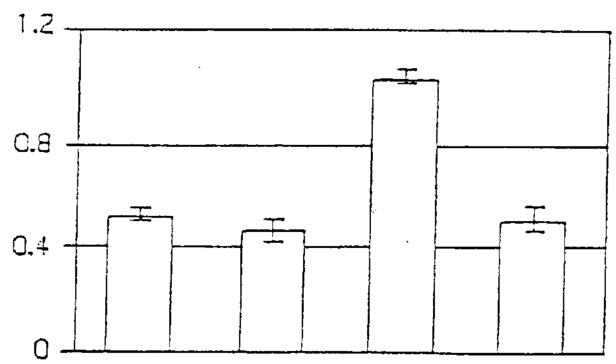
Figs. 7A-B

C
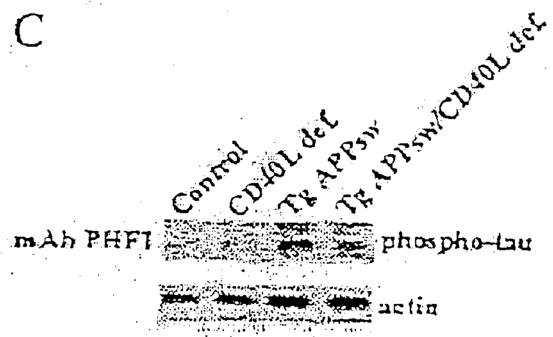
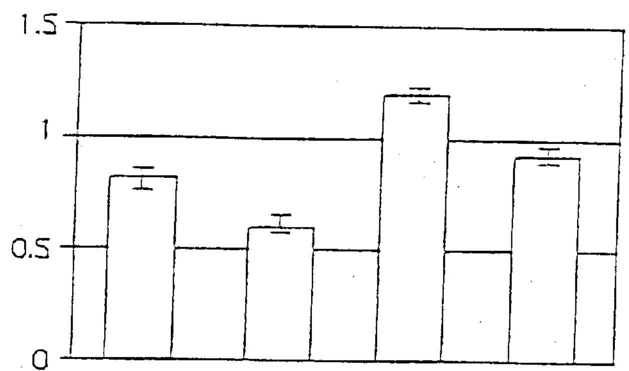
D
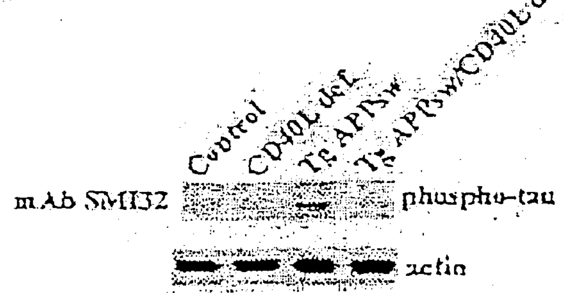
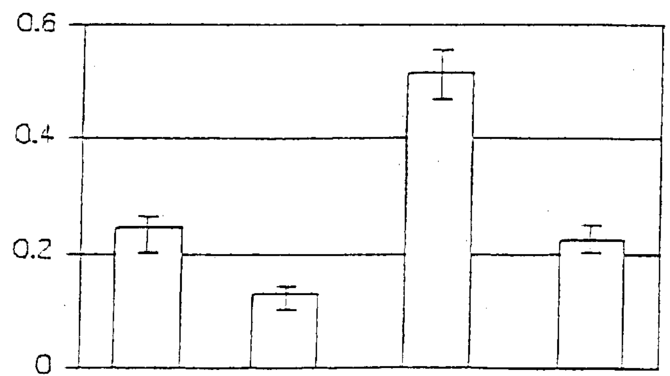
Figs. 7C-D 1.2
0.8
0.4
0

ASSAY FOR EVALUATING THE THERAPEUTIC EFFECTIVENESS OF AGENTS IN REDUCING ALZHEIMER'S DISEASE PATHOLOGY

CROSS REFERENCE TO RELATED APPLICATIONS

This is a conversion of U.S. Provisional Patent Application No. 60/137,016, filed Jun. 1, 1999, incorporated herein by reference.

TECHNICAL FIELD

The present invention relates to methods for treating Alzheimer's Disease (AD). More specifically, the present invention relates to methods of treating AD by inhibiting Aβ-induced microglial activation.

BACKGROUND ART

Alzheimer's disease (AD) is a neurodegenerative disease characterized by the presence of extracellular amyloid deposits (composed mainly of Aβ) and intraneuronal tangles (consisting of the cytoskeletal protein tau) in specific brain regions. Increased phosphorylation of tau is thought to result in neurofibrillary tangles in AD brains and with AD-like pathology in transgenic models of the disease [Genis et al., 1999; Schneider et al., 1999; Sturchler-Pierrat et al., 1997; James et al., 1996; Higgins et al., 1995].

The symptoms of AD include gradual loss of short-term memory, declined ability to perform routine tasks such as eating, confusion, disorientation, the inability of the patient to care for him or herself, and eventually death. The American Health Assistance Foundation has reported that, presently, more than four million Americans are believed to have AD. Furthermore, each year 250,000 new cases of AD are diagnosed and 100,000 Americans die because of AD. Moreover, one out of every ten Americans 65 years and older have AD and almost half of those 85 years and older have the disease.

The inflammatory component of AD is becoming increasingly substantiated as a major contributor to the AD pathogenic process. However, treatment strategies aimed at lessening the negative effects of inflammation in AD are only available to a very limited extent. Furthermore, rather than targeting AD-associated neuro-inflammation, these drugs tend to be general inhibitors of inflammation (such as non-steroidal anti-inflammatory agents like aspirin) which only provide partial therapeutic benefit (Rich, J. B., Rasmusson, D. X., Folstein, M. F., Carson, K. A., Kawas, C. & Brandt, J. Nonsteroidal anti-inflammatory drugs in Alzheimer's disease. *Neurology* 45, 51–55 (1995).

Amyloid β peptides (Aβ)have long been thought to be central to the neuropathology of Alzheimer's disease (AD) [Glenner and Wong, 1984]. Aβ peptides activate microglia, resident immune cells in the brain, resulting in markedly increased levels of the pro-inflammatory acute phase cytokine tumor necrosis factor-α (TNF-α release) [Meda et. al., 1999; Klegeris et. al., 1997]. At these high levels secreted by microglia, TNF-α has been shown to be neurotoxic (Tan et al., Journal of Neuroimmunology, 1999). For example, high doses (>11 μM) of $A\beta_{1-42}$ are able to produce increased TNF-α production in microglial cells [Meda et. al., 1999]. However, such doses of $A\beta_{1-42}$ rapidly produce large amounts of Aβ fibrils and loss of Aβ solubility in vitro [Castillo et al., 1997; Genis et al., 1999; Schneider et al., 1999; Sturchler-Pierrat et al., 1997; James et al., 1996; Higgins et al., 1995].

Previously, it has been suggested that Aβ activation of microglial cells may be involved in the inflammatory component of AD. The data indicate that Aβ can stimulate pro-inflammatory responses in microglia, including elevated cytokine release, nitric oxide synthase expression, nitric oxide production, and neurotoxicity [Meda, et al., 1995; Combs, et al., 1999; Kalaria, 1999]. However, the mechanisms of Aβ-induced microglial activation remain speculative, and often require a co-stimulatory factor such as the pro-inflammatory cytokine interferon-γ.

Since inflammatory processes are major contributors to AD pathophysiology and CD40, as an important cellular signaling and activation antigen, plays a key role in inflammatory processes [Schonbeck et al., 1997; Sempowski et. al., 1997; Karmann et. al., 1995], CD40 may play a key role in AD. Furthermore, as a neuroimmune response has previously been thought to be implicated in AD pathogenesis [Cacabelos R, Med Clin (Barc) Mar 26, 1994; 102(11): 420–2; McGeer P L, Rogers J, McGeer E G, Alzheimer Dis Assoc Disord 1994 Fall; 8(3): 149–58; Dickson, D W and Rogers, J, Neurobiol Aging 1992 November–December; 13(6): 793–8], and CD40 is functionally expressed on microglia [Tan et al., 1999, Journal of Neuroimmunology; Tan et al., 1999, Journal of Immunology], the possibility arises that CD40 may additionally mediate a pathogenic neuroimmune response in AD. However, it has not previously been established what, if any, role CD40 plays in the AD pathogenic process, nor how to utilize this knowledge in potential treatments of AD.

It would, therefore, be useful to determine the role that CD40 plays in AD. It would also be useful to develop methods for treating AD by modulating the CD40 pathway.

SUMMARY OF THE INVENTION

According to the present invention, there is provided an assay method for determining the effect of an agent on Alzheimer's Disease pathology by treating microglial cells with Aβ peptides, adding CD40 ligand to the microglial cells, adding a therapeutic agent to the microglial cells, and measuring Alzheimer's Disease pathology. Also provided is a method of determining therapeutic effectiveness of an agent for Alzheimer's Disease by measuring the inhibition of CD40–CD40L binding and/or its functional outcomes in the presence of the agent. A method of testing the efficacy of a therapeutic agent by producing Tg $APP_{sw}$ and Tg $APP_{sw}$/CD40L deficient mice and administering to these mice the therapeutic agent to be tested and determining the efficacy of the drug in suppressing Alzheimer's disease-like pathology is also provided. An assay for determining the effect of an agent on Alzheimer's Disease pathology by treating microglial cells with Aβ peptides, co-treating these cells with CD40 ligand, adding a therapeutic agent to the microglial cells and utilizing a measuring device for quantifying Alzheimer's Disease pathology is also provided.

BRIEF DESCRIPTION OF THE FIGURES

Other advantages of the present invention will be readily appreciated as the same becomes better understood by reference to the following detailed description when considered in connection with the accompanying drawings wherein:

FIGS. 1A–C are flow cytometric analyses of CD40 expression in control peptide or Aβ-treated microglial cells, which demonstrates that Aβ induces CD40 expression in N9 microglial cells, each histogram demonstrates the percentage of positive cells (CD40 expressing); the cell number (ordinate) vs. log fluorescence intensity (abscissa) using: FIG. 1A: 250 nM control peptide; FIG. 1B: 250 nM A$\beta_{1-40}$; FIG. 1C: 250 nM A$\beta_{1-42}$, results were obtained from five independent experiments. In addition, similar results were observed in N60 microglial cells. FIGS. 1E–F is a photograph showing primary hippocampal cultures from newborn mice (1–2 days old), isolated under sterile conditions and kept at 4° C. before mechanical dissociation; cells were plated in 75 cm2 flasks and complete medium was added; Primary cultures were kept for fourteen days; Glial cultures were then transferred onto glass slips, placed in 24-well plates and represent: FIG. 1E: Tg APP$_{sw}$ murine cultures stained with FITC-conjugated anti-CD40 (green) and PE-conjugated anti-CD11b (red) antibodies; and FIG. 1F: control murine cultures stained with FITC-conjugated anti-CD40 and PE-conjugated anti-CD11b antibodies; Yellow stain shows overlap between anti-CD40 and anti-CD11b antibodies; Similar results were obtained from three independent experiments;

FIGS. 2A–D are micrographs of primary cultured microglia treated with CD40L and A$\beta_{1-42}$ showing cortical neuron cell injury. Phase contrast views are shown before (top left) and after (bottom left) co-treatment with CD40L and A$\beta_{1-42}$, FIGS. 2A, 2B, respectively. Bright-field micrographs of identical fields are also displayed before (top right) and after (bottom right) co-treatment, FIGS. 2C, 2D, respectively. CD45 positive cells (brown) are microglia, while neurofilament L-staining cells (red) are neurons. The bar denotes 50 micrometers (calculated for each panel); Neuronal, but not microglial, degeneration is apparent only after co-treatment, and is not detectable following treatment with CD40L or A$\beta_{1-42}$ alone. Results shown are from one of three independent experiments with similar results.

FIG. 3A: shows that microglial activation is significantly reduced in primary cultured microglial cells from Tg APP$_{sw}$/CD40L deficient mice; RT-PCR shows increased expression of TNF-α mRNA in primary cultured microglia from Tg APP$_{sw}$ mice before and after CD40 ligation; the histogram represents TNF-α signal/actin signal, n=3 for each condition; Importantly, CD40 ligation of Tg APP$_{sw}$/CD40L deficient microglia raises TNF-α mRNA levels near that of Tg APP$_{sw}$ microglia. Before CD40 ligation, ANOVA revealed main effects of microglia from Tg APP$_{sw}$ (p<0.001) and CD40L deficient mice (p<0.02), as well as an interaction between them (p<0.02), indicating interactive blockade of TNF-α release in Tg APP$_{sw}$/CD40L deficient microglia. After CD40 ligation, ANOVA revealed significant main effects of microglia from Tg APP$_{sw}$ (p<0.01) and CD40L deficient mice (p<0.02), but no interaction between them (p>0.10), indicating recovery of the Tg APP$_{sw}$ phenotype in Tg APP$_{sw}$/CD40L deficient mice. FIGS. 3B–C: are bar graphs showing TNF-α release from microglia (pg/mg total protein)±1 SEM by TNF-α ELISA before (left) or after (right) CD40 ligation. Before CD40 ligation, ANOVA revealed main effects of microglia from Tg APP$_{sw}$ (p<0.001) and CD40L deficient mice (p<0.02), as well as an interaction between them (p<0.02), indicating interactive blockade of TNF-α release in Tg APP$_{sw}$/CD40L deficient microglia; After CD40 ligation, ANOVA revealed main effects of microglia from Tg APP$_{sw}$ (p<0.01) and CD40L deficient mice (p<0.02), but no interaction between them (p>0.10), indicating recovery of the Tg APP$_{sw}$ phenotype in Tg APP$_{sw}$/CD40L deficient microglia. FIG. 3C: is a bar graph showing TNF-α release from microglia (pg/mg total protein) ±1 SEM by TNFα ELISA after CD40 ligation. After CD40 ligation, ANOVA revealed main effects of microglia from Tg APP$_{sw}$ (p<.01) and CD40L deficient mice (p<.02), but no interaction between them (p<.10), indicating recovery of the Tg APP$_{sw}$ phenotype in Tg App$_{sw}$/CD40L deficient microglia.

FIGS. 7A–E: is a series of Western immunoblots showing that tau protein phosphorylation is significantly reduced in brains from Tg $APP_{sw}$ mice deficient for CD40L. FIG. 7A: shows that there was faster electrophoretic mobility of total tau (tau-1 and tau-2, region shown is from ~40 to 70 kDa), FIGS. 7B–E: show decreased phospho-tau signal 9 (region shown is from ~50 to 65 kDa) in brain lysates from Tg $APP_{sw}$/CD40L deficient mice compared to Tg $APP_{sw}$ animals. Western blots for identical samples were probed with the indicated tau-specific antibodies, stripped, and re-probed with actin antibody (above); histogram representing the ratio of total or phospho-tau to actin signal (below), with n=3 for each group. For phospho-tau antibodies, ANOVA revealed main effects of Tg $APP_{sw}$ status ($p<0.001$) and CD40L deficiency ($p<0.001$); Furthermore, there was a statistical interaction between Tg $APP_{sw}$ status and CD40L deficiency ($p<0.01$), suggesting that CD40L is on the mediating pathway to tau phosphorylation; One-way ANOVA revealed between-group differences ($p<0.001$), and post-hoc comparison showed differences between brains from control littermates and Tg $APP_{sw}$ ($p<0.001$) animals, as well as between Tg $APP_{sw}$ and Tg $APP_{sw}$/CD40L deficient brains ($p<0.001$).

DETAILED DESCRIPTION OF THE INVENTION

Figure 1D:
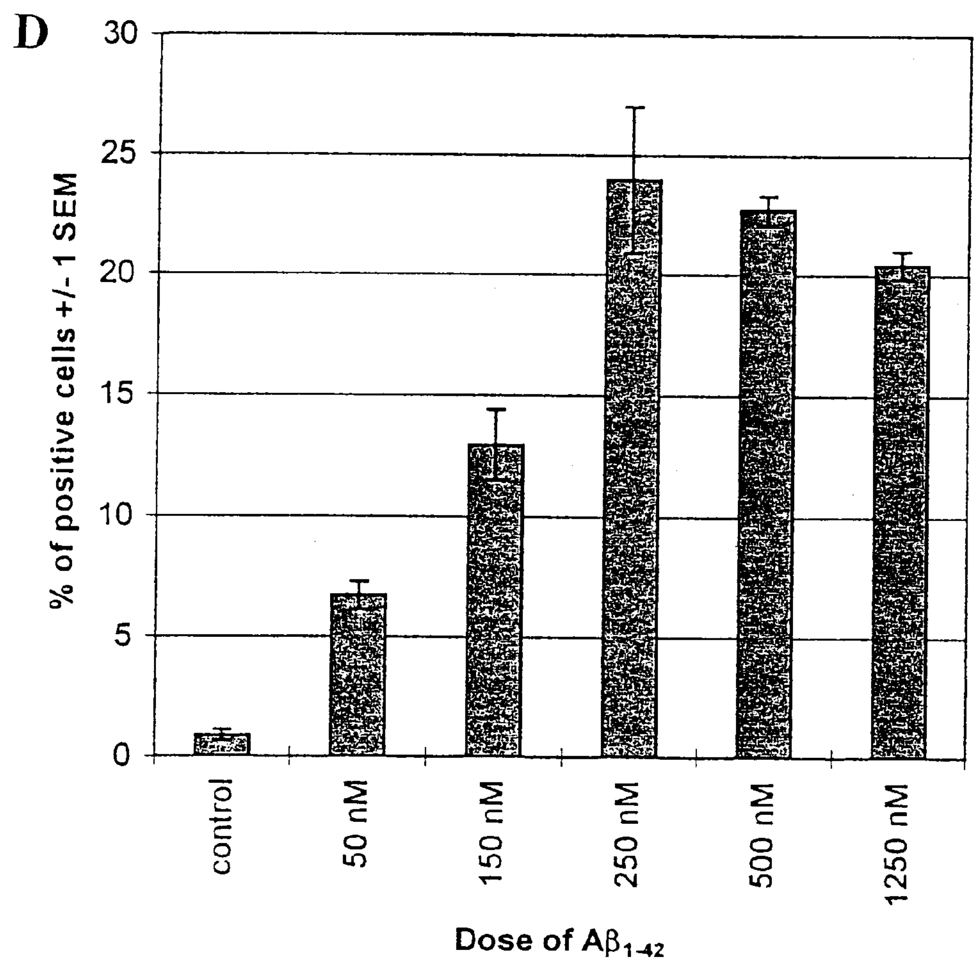
FIG. 1D: is a bar graph showing that Aβ induces microglial CD40 expression in a dose-dependent manner, each bar represents percentage of positive cells (CD40) expressing N9 microglial cells after treatment with various doses of A$\beta_{1-42}$; data shown are represented as mean percentages±1 SEM. N=9 for control peptide, 250 nM; n=6 for A$\beta_{1-42}$, 250 nM; n=3 for all other treatment conditions; A$\beta_{1-42}$ dose is a significant effect (p<0.001) by ANOVA.

Generally, the present invention provides a method and assay for determining the therapeutic effectiveness of an agent on the neuropathology of Alzheimer's Disease. More specifically, the present invention provides a method and treatment of Alzheimer's Disease by inhibiting CD40-mediated, Aβ-induced microglial cell activation.

By "therapeutic agent" it is meant an agent which is effective in inhibiting Alzheimer's Disease pathology. More specifically, the therapeutic agent will suppress and/or alter some or all of the following:

neurodegeneration, Aβ plaque deposition, APP metabolism, Aβ levels, neuroinflammation, cerebrovascular pathology, microglial/astrocyte activation, and behavioral/cognitive impairment associated with Alzheimer's Disease. For example, such agent can be useful in blocking the CD40 interaction and binding with CD40L and/or modulating the outcomes of CD40 pathway stimulation. Examples of potential therapeutic agents include antibodies, compounds belonging to the class of anti-inflammatory agents, compounds which oppose immune cell activation, compounds which alter the intracellular CD40 or CD40L signaling pathway and compounds which block the CD40–CD40L interaction.

A measuring device is also provided by the present application. This measuring device is useful in measuring Alzheimer's Disease pathology. Preferably, Alzheimer's Disease pathology is measuring utilizing microglial activation, increased phosphorylation of tau protein, and neuronal cell injury. This list is not intended to be exhaustive and can include other measuring devices known to those with skill in the art.

Specifically, when measuring microglial activation, the preferred embodiments involve determining the amount of TNF-$\alpha$ production, nitric oxide production, inducible nitric oxide synthase, microglial glutamate production and microglial induced neuronal injury. These measurements can be made using Western immunoblotting, ELISA, LDH release assay, $^{51}$Cr release assay, microscopy, and biochemical reactions (for nitric oxide measurement). However, other determinations can be utilized as are known to those of skill in the art. When measuring hyperphosphorylation of tau, the preferred embodiment involves Western immunoblotting and/or immunohistochemistry utilizing antibodies specific for phosphorylated epitopes on tau. Measuring the neuronal cell injury associated with Alzheimer's Disease can preferably be determined using a number of different tests including, but not limited to, LDH release, chromium release, and microscopically.

In the preferred embodiment, the therapeutic agent is selected to block CD40-mediated, Aβ-induced microglial cell activation or to alter the intracellular CD40 or CD40L signaling pathway. This is useful in suppressing associated neurodegeneration of Alzheimer's Disease in vivo. Specifically, the therapeutic agent blocks the CD40 interaction with CD40L and/or the functional outcomes of this interaction. It is this interaction which is the beginning of the signaling pathway which leads to Alzheimer's disease-like neurodegeneration. Therefore, by blocking the CD40 pathway the therapeutic agent suppresses neurodegeneration associated with Alzheimer's Disease.

In order to determine the CD40 patherway, cultured human aortic endothelial cells (HAEC) were incubated with freshly solublized Aβ and then the expression of a central immunoregulatory molecule, CD40, were examined in these cells using RT-PCR, Western immunoblotting and Flow cytometry. The results show that treatment of endothelial cells with $A\beta_{1-40}$, $A\beta_{1-42}$ or IFN-$\gamma$ results in a dose-dependent induction of endothelial CD40 expression. Furthermore, ligation of endothelial CD40 and simultaneous treatment of human endothelial cells with IFN-$\gamma$ or Aβ peptides leads to a significant release of IL-1β, a marker for endothelial cell activation. Since IL-1β is an important inflammatory response mediator, these findings show that the functional role of Aβ-induced endothelial CD40 is promotion of the inflammatory cascade in vascular endothelial cells. Since IL-1 beta is also, like TNF-alpha, a pro-inflammatory cytokine that has been implicated in neuronal injury, there is established a connection between the results of the endothelial cell experiments and those of the microglial cells. Therefore, CD40 activation could play a role in the inflammatory pathway resulting in vascular endothelium dysfunction, although the cellular mechanisms mediating this effect is different than those in lymphocytes.

The possible role of CD40 in Aβ-mediated endothelial cell inflammation was examined. Treatment of human aortic endothelial cells with relevantly low doses of IFN-$\gamma$ or freshly solublized $A\beta_{1-40}$ or $A\beta_{1-42}$ leads to significant expression of CD40. Further, ligation of endothelial CD40 with CD40L results in a significant release of IL-1β, confirming that CD40 expression is functional. Since IL-1β is an important pro-inflammatory cytokine, these results show a novel basis by which the CD40–CD40L interaction could promote dysfunction in Alzheimer-vascular endothelium.

Applicants have demonstrated that Aβ activation of microglial cells increases CD40 expression and that CD40 binding to CD40L results in bystander-induced neuronal cell injury, thereby demonstrating that Aβ-induced CD40 signaling can promote AD-like pathology.

The present invention recognizes, for the first time, an association between Aβ peptides and CD40-mediated microglial activation, enhanced expression of CD40 with low doses Aβ (250–1000 nM, $A\beta_{1-40}$, $A\beta_{1-42}$), and interaction between CD40 and CD40L on microglia resulting in microglia-induced and neuronal cell injury. Thus, it is demonstrated herein that the Aβ/CD40 signaling pathway can result in AD-like pathology.

The present invention recognizes that blocking CD40 and CD40L binding opposes the AD-like pathology in a mouse model of the disease. Therefore, it is herein demonstrated an assay method to examine the ability of numerous therapeutic agents to block the Aβ/CD40 signaling pathway thus suppressing AD pathology. The present invention further recognizes that blocking CD40 and CD40L binding alters the AD pathogenic process. Thereby demonstrating an assay method to examine the ability of numerous therapeutic agents to block the CD40 signaling pathway thus suppressing AD neurodegeneration.

The present invention provides an assay method for determining the effect of an agent on Alzheimer's disease pathology. This assay method includes the steps as follows: a. treating microglial cells with Aβ peptides; b. adding CD40 ligand (CD40L) to the microglial cells; c. adding a therapeutic agent to the microglial cells, and d. measuring the Alzheimer's disease pathology. In the preferred embodiment the therapeutic agent is an antibody however other compounds can also be used without departing from the heart of the present invention. For example, the compounds can include, but are not limited to inorganic compounds, organic compounds, peptides, peptide libraries, chemical libraries and chiral libraries.

Also provided by the present invention is a method of determining therapeutic effectiveness of an agent for Alzheimer's disease by measuring the inhibition of the CD40–CD40L binding and/or the functional outcomes of CD40 pathway modulation in the presence of the agent. The potential agents are set forth above.

The present invention also provides a method of treating Alzheimer's disease by blocking Aβ-induced microglial cell activation. In the preferred embodiment this blocking requires blocking the CD40 interaction with CD40L using an agent. As set forth previously, this agen can be an antibody, however other compounds can also be used without departing from the heart of the present invention. For example, the compounds can include, but are not limited to inorganic compounds, organic compounds, peptides, peptide libraries, chemical libraries and chiral libraries.

Additionally, the present invention provides a method of testing the efficacy of a therapeutic agent by producing a Tg $App_{sw}$/CD40L deficient mouse. Next, the therapeutic agent to be tested is administered to the mouse. Then, the efficacy of the drug in suppressing pathology associated with Alzheimer's Disease is determined using the assays and methods set forth above.

An assay for determining the effect of an agent on Alzheimer's Disease pathology is also provided by the present invention. This assay includes Aβ peptides which are added to microglial cells, CD40 ligand which is also added to the microglial cells, a therapeutic agent for being added to the microglial cells; and a measuring device for quantifying Alzheimer's Disease pathology. The measuring devices depend on the therapeutic agent used. A list of therapeutic agents and devices are set forth above. This list is not exhaustive and is for illustrative purposes, other therapeutic agents and devices can be used as are known to those of skill in the art.

The above discussion provides a factual basis for the use of a therapeutic agent for suppressing the neurodegeneration associated with Alzheimer's Disease. The methods used with and the utility of the present invention can be shown by the following non-limiting examples and accompanying figures.

EXAMPLES

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., Recombinant DNA, Scientific American Books, New York and in Birren et al (eds) *Genome Analysis: A Laboratory Manual Series*, Vols. 1–4 Cold. Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: *A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Western Immunoblotting

Western immunoblots can be used to quantify amounts of specific proteins in cell/tissue lysates. This method provides a rapid and sensitive screen of such proteins, and, therefore, is another preferred immunoassay by those skilled in the art. As an example of this method, we have used this method to quantify CD40 expression on cultured HAEC. Cultured HAEC were plated at $1 \times 10^6$ cells/well in 100 mm culture dishes (Falcon, Becton Dickinson Inc. New Jersey). HAEC were treated with freshly solubilized $A\beta_{1-40}$, or $A\beta_{1-42}$, (5 mM, in $dH_2O$), control peptide (5 $\mu$M), IFN-γ (100 U/mL), or untreated (Aβ-free) for 48 hours after plating. Cells were washed in ice-cold phosphate buffered saline (PBS) three times and lysed in an ice-cold lysis buffer containing 0.2 mM EDTA, 20 mM Tris/HCl (pH 8.0), 100 mM NaCl, 3% Nonidet P-40, 50 mM NaF, 10 mM sodium pyrophosphate, 2 mM orthovanadate, 10 $\mu$g/mL each of aprotinin and leupeptin and 1 mM PMSF. After incubation for thirty minutes on ice, samples were centrifuged at 15,000 rpm for fifteen minutes, and supernatants were collected. Total protein content was estimated using the Bio-Rad protein assay.

An aliquot corresponding to 50 $\mu$g of total protein of each sample was separated by SDS-PAGE and transferred electrophoretically to Hy-bond PVDF membranes (Bio-Rad, California). Nonspecific antibody binding was blocked overnight at 4° C. with 5% non-fat dry milk in TBS (20 mM Tris, 500 mM NaCl, pH 7.5). Immunoblotting was carried out with a polyclonal rabbit anti-human CD40 antibody (Santa Cruz Biotechnology, California) followed by an anti-rabbit alkaline phosphatase-conjugated IgG secondary antibody (Santa Cruz Biotechnology, California) as a tracer. The Immun-Star chemiluminescence substrate (Bio-Rad, California) was used in the development of the blots. Blots were also carried out on identical membranes with a reference anti-actin mouse monoclonal antibody (Boehringer Mannhem), which allowed for semi-quantitative CD40 protein determination. Densitometric analysis was performed for protein bands using the Fluor-S™ MultiImager with Quantity One™ software (Bio-Rad, California).

Antibody Production

Antibody Production: Antibodies can be either monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W.H. Freeman and Co., 1992. Antibody fragments can also be prepared from the antibodies and include Fab, $F(ab')_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$ and iodination.

Recombinant Protein Purification

Marshak et al, "Strategies for Protein Purification and Characterization. A laboratory course manual." CSHL Press, 1996.

Transaenic and Knockout Methods

The present invention provides for transgenic gene and polymorphic gene animal and cellular (cell lines) models as well as for knockout models. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

For Gene Therapy:

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the hostipatient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle can include elements to control targeting, expression and transcription of the nucleic acid in a cell selective manner as is known in the art. It should be noted that often the 5'UTR and/or 3'UTR of the gene can be replaced by the 5'UTR and/or 3'UTR of the expression vehicle. Therefore as used herein the expression vehicle can, as needed, not include the 5'UTR and/or 3'UTR of the actual gene to be transferred and only include the specific amino acid coding region.

The expression vehicle can include a promotor for controlling transcription of the heterologous material and can be either a constitutive or inducible promotor to allow selective transcription. Enhancers that can be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), Vectors: *A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

Delivery of Gene Products/therapeutics (Compound):

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses can be single doses or multiple doses over a period of several days, but single doses are preferred.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

Example 1

To determine whether Aβ could induce CD40 expression in cultured N9 and N60 microglial cells, cells were treated with 250 nM of freshly solublized $A\beta_{1-40}$ or $A\beta_{1-42}$. As shown in both FIGS. 2A–D, both $A\beta_{1-40}$ and $A\beta_{1-42}$ significantly induce CD40 expression on cultured microglial cells when compared to Aβ-free, reverse Aβ ($A\beta_{40-1}$) or the 695 isoform of soluble amyloid precursor protein (sAPPα-695) when compared to control peptide (human thyrocalcitonin) or Aβ free conditions. In addition, $A\beta_{1-42}$ induced microglial CD40 expression in a dose dependent manner (from 50 to 1250 nM, FIG. 2E).

To determine whether endogenous overexpression of Aβ could lead to microglial CD40 expression, CD40 expression on microglia was measured from a transgenic mouse model of AD (Tg $APP_{sw}$, overexpressing $A\beta_{1-40}$ and $A\beta_{1-42}$), (11) and control (wild-type) littermates (12). Microglia from Tg $APP_{sw}$ newborn mice had markedly increased levels of soluble $A\beta_{1-40}$ compared to control littermates (13), and the CD40-expressing cell fraction is markedly increased in primary cultured microglia from Tg $APP_{sw}$ mice compared to microglia from control littermates (14). CD40 expression is increased in microglia from control littermates exposed to $A\beta_{1-42}$, and in Tg $APP_{sw}$ microglia re-exposed to exogenous $A\beta_{1-42}$ compared with $A\beta_{40-1}$ or sAPPα-695 (14). These data show that Aβ peptides specifically induce CD40 expression in primary cultured and N9 microglia.

To examine whether pro-inflammatory cytokines could regulate Aβ-dependent CD40 expression, Aβ-challenged microglia were treated with low doses of IL-1b, IL-2, IL-4, IL-6, IL-12 or IFN-γ (15), as the expression of CD40 has been shown to be variously regulated by these cytokines on human thymic epithelial cells, human endothelial cells and keratinocytes (16). Only a low dose (10 U/mL) of IFN-γ synergistically enhances Aβ-dependent CD40 expression on cultured microglial cells (17). Mononuclear cells from AD patients secrete markedly higher levels of IFN-γ compared to age-matched controls (18). Furthermore, increased levels of IFN-γ have been shown to activate microglia following stimulation with Aβ (1). The data show that IFN-γ increases Aβ's effect on activation of microglia through induction of the CD40 receptor.

Activation of microglial cells results in an increase in TNF-α release (1, 19) and high doses (>11 μM) of $A\beta_{1-42}$ are able to produce increased TNF-α production in microglial cells (1). Such doses of $A\beta_{1-42}$ rapidly produce large amounts of Aβ fibrils and loss of Aβ solubility in vitro (20). A much lower dose of freshly solubilized $A\beta_{1-42}$ (500 nM) does not induce TNF-α release from primary cultured microglia (21,22). However, when cultured microglia are pre-treated with the same low dose of $A\beta_{1-42}$, the addition of CD40L synergistically increases TNF-α release (22). Using a monoclonal antibody to CD40, which extinguishes CD40L-induced TNF-α release in a dose-dependent manor, the CD40–CD40L interaction was attenuated in microglia and TNF-α release was significantly reduced after $A\beta_{1-42}$ treatment (22). This result indicates that CD40L mediates its effects via the CD40 receptor.

Figure 2E:
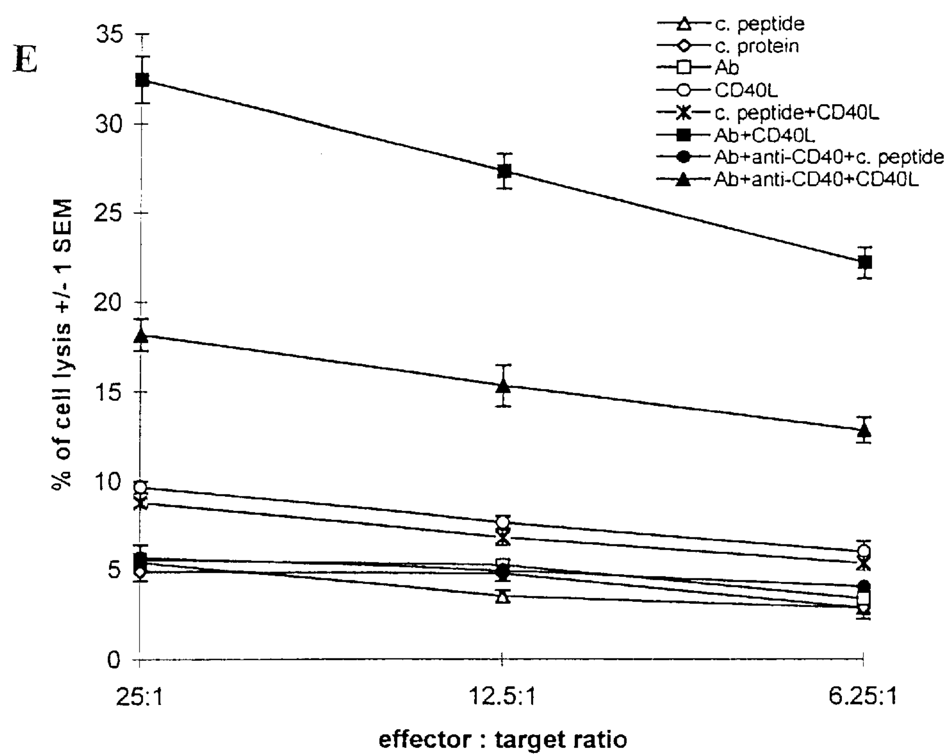
FIG. 2E is a graph showing primary cultured microglia-mediated neuronal cell injury as evidenced by $^{51}$Cr release. Data are reported as mean $^{51}$Cr release values±1 SEM and n=9 for each condition presented. ANOVA showed main effects of effector: target ratio (p<0.001), CD40L (p<0.001), anti-CD40 antibody (p<0.001) and A$\beta_{1-42}$ (p<0.001), but not for reverse A$\beta_{40-1}$ (p<0.752); ANOVA also revealed an interactive term among A$\beta_{1-42}$, CD40L and effector: target ratio (p<0.001), indicating a ratio-dependent decrease in percentage of cell lysis as a result of the interaction between A$\beta_{1-42}$ and CD40L. Post-hoc comparison showed a difference across ratios between A$\beta_{1-42}$+CD40L and A$\beta_{1-42}$+anti-CD40+CD40L experimental conditions (p<0.001), indicating an overall decrease in percentage of cell lysis as a result of addition of the anti-CD40 antibody.
Figure 2F:
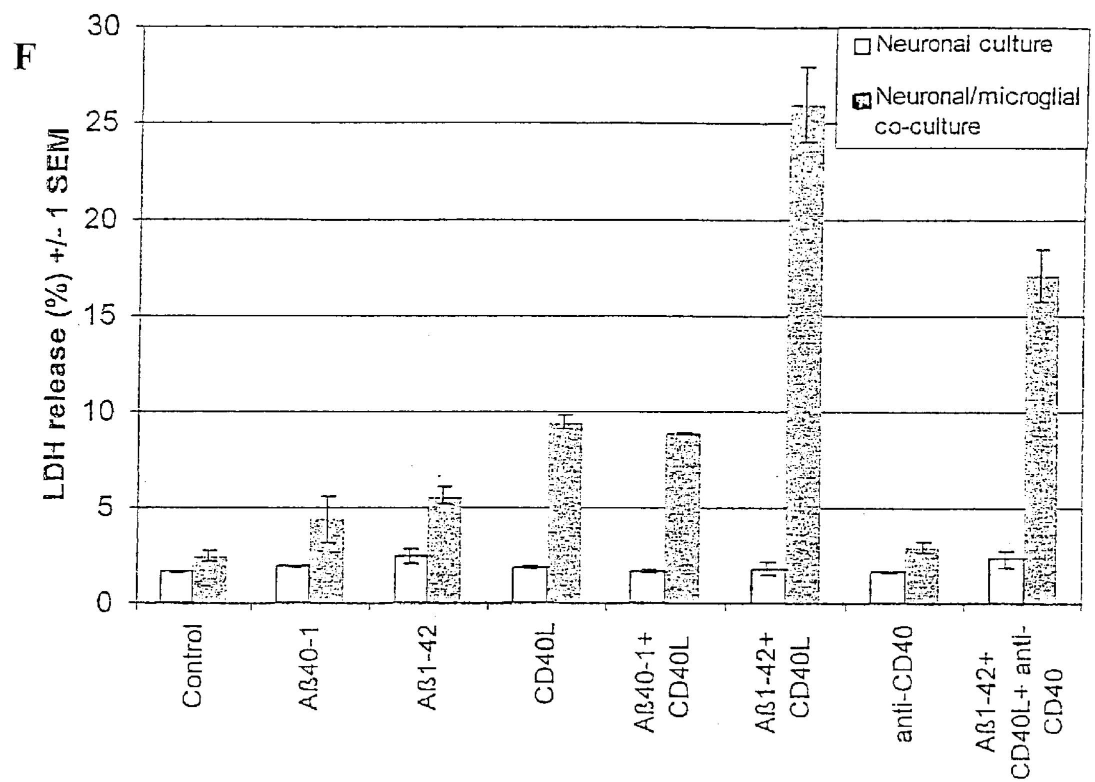
FIG. 2F is a bar graph showing microglia-mediated neuronal cell injury by the percent release of LDH ±1 SEM, and results are similar to those in the $^{51}$Cr release assay; again, A$\beta_{1-42}$+CD40L demonstrated significant cell injury when compared to A$\beta_{40-1}$, A$\beta_{1-42}$, CD40L, A$\beta_{40-1}$ and CD40L, anti-CD40L. The addition of anti-CD40 to A$\beta_{1-42}$+CD40L resulted in a decrease in cell injury as measured by LDH release. N=9 for each condition presented.

Having shown that Aβ peptides activate microglia through the CD40 pathway, it was then investigated whether activation of Aβ-pretreated microglia by ligation of CD40 could mediate neuronal cell injury (23,24). Activated microglial cells (resulting from $A\beta_{1-42}$ followed by CD40L treatment) promote injury of primary cultured cortical neurons (FIG. 2A). Interestingly, exogenous TNF-α, at similar levels as those produced by microglia, activated with $A\beta_{1-42}$ and CD40L dose-dependently induces neuronal injury and death as measured by LDH release assay (25), suggesting a mechanism by which the CD40–CD40L interaction is responsible for the effect. Blockade of CD40 with anti-CD40 antibody (1:200 dilution) significantly reduces neuronal cell injury (FIGS. 2E, 2F) showing that the interaction of CD40L with CD40 on Aβ-pretreated microglia is crucial for induction of neuronal injury.

To evaluate the possibility that Aβ leads to CD40 pathway-mediated microglial activation in vivo, Tg $APP_{sw}$ mice were crossed with mice deficient in CD40L (26), and TNF-α production was measured in primary cultured microglial cells from these animals (27). Results show increased production of TNF-α mRNA and protein in microglia from Tg $APP_{sw}$ mice compared to control littermates (FIG. 3A). Furthermore, TNF-α production is significantly attenuated in Tg $APP_{sw}$/CD40L deficient microglia compared to Tg $APP_{sw}$ microglial cells (FIG. 3B), showing that attenuation of the CD40–CD40L interaction results in reduced microglial activation in a transgenic model of AD. Moreover, re-challenge of Tg $APP_{sw}$/CD40L deficient microglia with CD40L results in recovery of the Tg $APP_{sw}$ phenotype (FIG. 3C), further confirming the requirement of CD40 pathway stimulation in mediating Aα's bioactive response.

Figure 7E:
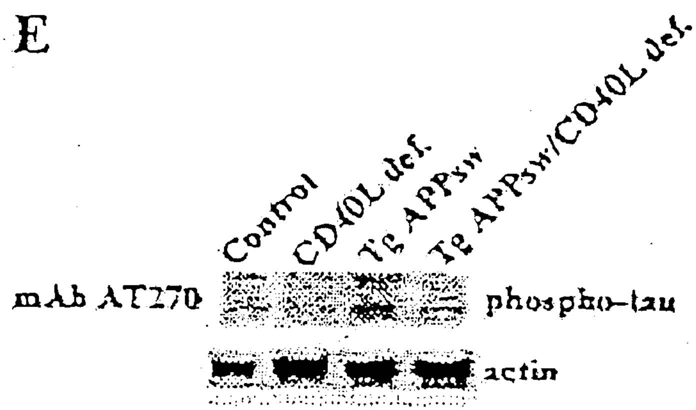

The data thus far shows that Aβ initiates microglial activation through the CD40 pathway, an effect which was attenuated in transgenic APP mice deficient for CD40L. In order to assess the possibility that the Ab–CD40–CD40L pathway might be an early stimulant of pathology associated with AD, tau phosphorylation status was examined in the transgenic mice, hyperphosphorylation of which is known to be associated with neurofibrillary tangles in AD brains and with AD-like pathology in transgenic models of the disease (28). Brain homogenates from Tg $APP_{sw}$ mice deficient for CD40L demonstrate both a faster tau electrophoretic mobility (FIG. 7A) and a significant reduction in phospho-tau immunoreactivity at multiple sites by Western immunoblotting compared to Tg $APP_{sw}$ mice alone (29, FIGS. 7B–E). All of the animals in these experiments were eight months old, an age before which significant Aα deposition occurs in the Tg $APP_{sw}$ mouse line employed (11), showing that these events occur early in the processes which mediate AD neuropathology.

There are three possible scenarios for how microglial activation can occur in AD. In AD it has been shown that activated microglia are co-localized with perivascular Aβ (30), and endothelial and smooth muscle cells constitutively express CD40L at low levels (31). The activation of perivascular microglia can result from an interaction between the smooth muscle or endothelial cell-derived CD40L and Aα-dependent microglial CD40. Further, perivascular microglial activation can contribute to the perivascular neuronal cell death that occurs in AD and the vascular damage associated with cerebral amyloid angiopathy which occurs in 83% of AD cases (32). T cell-associated antigens have been found in AD brains, and activated T cells have been found in AD brain tissue closely associated with reactive microglia (33). As activated CD4+ T cells express CD40L, it is possible that activated T cells are able to provide CD40L for the activation of microglia. Finally, a recent study reported that activated platelets express CD40L (34), and activation of platelets is increased in AD patients (35). These findings raise the possibility that Aα-induced CD40-expressing microglial cells receive CD40L from activated platelets.

Taken together, the data demonstrates how low doses of Aβ lead to microglial activation only after ligation of CD40. Previous findings have shown that Aβ can act directly on neurons to promote oxidative stress and increase their vulnerability to excitotoxicity and apoptosis. The present findings suggest that, in addition to such direct actions on neurons, Aβ can indirectly endanger neurons by inducing microglial responsiveness to CD40 ligand, resulting in the production of neurotoxic molecules by microglia. Noteworthy is the finding that Tg $APP_{sw}$ mice do not demonstrate marked neuronal cell loss (11), as opposed to the in vitro data showing Aβ-induced, microglial CD40-mediated neuronal degeneration. This difference is due to other cell types (including astroglia and cerebral vascular cells) and extracellular systems available in vivo in the CNS which are likely to mitigate against the tendency to neuronal death induced by Aβ and CD40L. In the experimental models, the CD40-mediated neurotoxic pathway is activated quite early in the pathogenic cascade, showing that therapeutic agents that suppress the CD40 signaling pathway can prove effective in suppressing the neurodegenerative cascade.

Example 2

Materials and Methods

Endothelial Cell Culture and Reagents

HAEC and HAEC medium were purchased from Clonetics (San Diego, Calif.). HAEC were cultured and expression assays were performed as previously described [29]. $A\beta_{1-40}$, $A\beta_{1-42}$, and reverse $A\beta_{40-1}$, (control) peptides were obtained from QCB (Hopkinton, Mass.). Reverse transcriptase polymerase chain reaction (RT-PCR) kits and RNA reagents were obtained from Invitrogen Inc. (San Diego, Calif.). Human IFN-γ recombinant protein was purchased from Genzyme (Cambridge, Mass.).

RT-PCR

Cultured HAEC were plated at $1\times10^5$ cells/well in 6-well culture plates (Falcon, Becton Dickinson Inc. New Jersey). HAEC were treated with freshly solubilized $A\beta_{1-40}$, or $A\beta_{1-42}$, (500 nM, in $dH_2O$), control peptide (500 nM) or IFN-γ (10 U/mL) for 48 hours after plating. Total RNA was isolated, and cDNA was prepared as previously described [30]. PCR was performed for 30 cycles, with each cycle consisting of 94° C. for one minute, 55° C. for two minutes, and 72° C. for two minutes, followed by a final extension step at 72° C. for ten minutes. Forward (5'-CCT GGC CTC ACC TCG CCA TGG-3') (Seq. ID. No. 1) and reverse (5'-GAG GGG CTG GCA CTG ACT GGG-3') (Seq. ID. No. 2) oligbnucleotides [28] were designed to produce the partial 974 bp human CD40 cDNA. Another RT-PCR was performed on identical samples for reference comparison using a primer pair specific for γ-actin (forward, 5'-CAG AGG CTC CCC TAA ATC CC-3' (Seq. ID. No. 3); reverse, 5'-CAC ACT GAG TAC TTG CGC TC-3') (Seq. ID. No. 4) which yields the 702 bp γ-actin cDNA fragment [23].

Western Immunoblotting

Cultured HAEC were plated at $1\times10^6$ cells/well in 100 mm culture dishes (Falcon, Becton Dickinson Inc. New Jersey). HAEC were treated with freshly solubilized $A\beta_{1-40}$, or $A\beta_{1-42}$, (5 mM, in $dH_2O$), control peptide (5 μM), IFN-γ (100 U/mL), or untreated (Aβ-free) for 48 hours after plating. Cells were washed in ice-cold phosphate buffered saline (PBS) three times and lysed in an ice-cold lysis buffer containing 0.2 mM EDTA, 20 mM Tris/HCl (pH 8.0), 100 mM NaCl, 3% Nonidet P-40, 50 mM NaF, 10 mM sodium pyrophosphate, 2 mM orthovanadate, 10 μg/mL each of aprotinin and leupeptin and 1 mM PMSF. After incubation for thirty minutes on ice, samples were centrifuged at 15,000 rpm for fifteen minutes, and supernatants were collected. Total protein content was estimated using the Bio-Rad protein assay. An aliquot corresponding to 50 μg of total protein of each sample was separated by SDS-PAGE and transferred electrophoretically to Hy-bond PVDF membranes (Bio-Rad, California). Nonspecific antibody binding was blocked overnight at 4° C. with 5% non-fat dry milk in TBS (20 mM Tris, 500 mM NaCl, pH 7.5). Immunoblotting was carried out with a polyclonal rabbit anti-human CD40 antibody (Santa Cruz Biotechnology, California) followed by an anti-rabbit alkaline phosphatase-conjugated IgG secondary antibody (Santa Cruz Biotechnology, California) as a tracer. The Immun-Star chemiluminescence substrate (Bio-Rad, California) was used in the development of the blots. Blots were also carried out on identical membranes with a reference anti-actin mouse monoclonal antibody (Boehringer Mannhem), which allowed for semi-quantitative CD40 protein determination. Densitometric analysis was performed for protein bands using the Fluor-S™ MultiImager with Quantity One™ software (Bio-Rad, California).

Flow Cytometric Analysis

Cultured HAEC were treated as described above. For fluorescence-activated cell sorter (FACS) analysis, $1\times10^6$ HAEC [Aβ-free, freshly solubilized $A\beta_{1-40}$, or $A\beta_{1-42}$, treated (500 nM0, control peptide-treated (500 nM) or IFN-γ-treated (10 U/mL)] were resuspended in 200 μl of 1×PBS and were incubated at 4° C. for thirty minutes with 10 μL of a 0.5 mg/mL stock solution of either FITC labeled anti-human CD40 antibody (PharMingen, Los Angeles, Calif.) or FITC labeled anti-human IgG1 control antibody (PharMingen, Los Angeles, Calif.). Following incubation, cells were washed in 3 mL of 1×PBS and resuspended in 200 μL of 1×PBS containing 2% paraformaldehyde and 0.1% $NaN_3$. Cells were analyzed on a FACScan flow cytometer (Becton-Dickinson, Mountain View, Calif.) using LYSIS-II software. CD40-expressing cells are defined as percentage of CD40-staining cells minus the percentage of IgG1-staining cells.

CD40 Cell ELISA

To determine if CD40 expression on cultured HAEC was IFN-γ or Aβ dose-dependent, CD40 cell ELISA assays were performed according to published procedures [4,12]. Briefly, cultured HAEC were plated at $2\times10^4$ cells/well in flat-bottom, 96-well tissue culture plates (Nunc-Immuno™ Plate, Denmark). Certain HAEC were treated with a dose range (50 nM to 10,000 nM) of freshly solubilized $A\beta_{1-40}$, $A\beta_{1-42}$, or control peptide. Other HAEC were treated with a dose range (5 U/mL to 500 U/mL) of IFN-γ. Primary cultured human renal carcinoma cells (HRCC), which do not express CD40, a control was used and was subjected to a dose range of $A\beta_{1-40}$. Forty-eight hours post-treatment, plates were fixed overnight at 4° C. in 1% paraformaldehyde diluted in 1×PBS, washed three times with wash buffer (0.5% Tween 20 in 1×PBS), and subsequently incubated with 200 mL of blocking buffer (10% fetal bovine serum in wash buffer) for one hour at 37° C. Cells were then treated with purified anti-human CD40 antibody (5 mg/ml, PharMingen, Los Angeles, Calif.) in 100 mL of blocking buffer for one hour at 37° C. Plates were washed four times with wash buffer. Biotinylated anti-mouse IgG1 (PharMingen, Los Angeles, Calif.; 1:2,000 dilution in blocking buffer, 100 ml/well) was added and incubated for one hour at 37° C., followed by the addition of 100 mL of a 1:3,000 dilution of HRP-Streptavidin (ZYMED, San Francisco, Calif.) for thirty minutes at 37° C. Plates were washed 4× with wash buffer and developed for twenty minutes at room temperature using the 3, 3', 5, 5'-tetramethylbenzidine (TMB) one-step substrate system (DAKO, Carpinteria, Calif.) followed by the addition of 100 μL/well of 2N $H_2SO_4$ to stop the reaction. Absorbance was measured at 450 nm using a microplate spectrophotometer (SPECTRAmax 250, Molecular Devices, Sunnyvale, Calif.). After measurement of absorbance, cell numbers in each treatment group were counted, and ANOVA did not reveal significant between-treatment groups difference s(F (3,59)=1.65, p=0.187).

Human IL-1β Release Elisa

To examine if endothelial CD40 would be functional, cultured HAEC were plated at $5\times10^4$ cells/well in 6-well tissue culture plates (Nunc-Immuno™ Plate, Denmark) and incubated at 37° C. with human CD40L recombinant protein (CD40L, 0.5 ug/mL, kindly provided by Dr. Jean-Yves Bonnefoy, Glaxo Institute for Molecular Biology, Geneva) in fresh cultured media for eight hours, and cell-free supernatants were collected for IL-1β release assay. The assay for human IL-1β was performed in strict accordance with the manufacturer's instruction using the human Predicta™ IL-1β Kit (Genzyme). Absorbance at 450 nm was measured using a microplate spectrophotometer (SPECTRAmax 250, Molecular Devices, Sunnyvale, Calif.).

Statistical Analysis

Analysis of variance (ANOVA) was used to analyze the data, followed by Tukey's or Scheffe's post-hoc comparison where appropriate for multiple mean comparisons. A test for independent samples was used for single mean comparisons. Standard errors of the mean (SEs) were calculated according to standard procedures. Alpha levels were set at 0.05 for each analysis. All analyses were performed using SPSS for windows release 7.5.

RESULTS

ADβ Induces CD40 mRNA Expression in Cultured HAEC

It has been shown that CD40 is constitutively expressed in cultured endothelial cells at low levels, which is regulated by cytokines, such as IFN-γ[17,19]. In order to investigate whether endothelial CD40 could be regulated in vitro by Aβ peptides, CD40 mRNA were analyzed in cultured HAEC following stimulation with 500 nM of either $A\beta_{1-40}$, or $A\beta_{1-42}$ (near the dose there was previously observed vascular endothelium dysfunction [32]) using RT-PCR. Results showed that CD40 mRNA expression was markedly increased in HAEC treated with $A\beta_{1-40}$, or $A\beta_{1-42}$ treatment resulted in an approximate 50–70% increase in the mRNA level of endothelial CD40 observed over the endogenous signal observed in response to control peptide treatment (FIG. 1D).

Aβ-induced Endothelial CD40 is Detected by Western Immunoblotting and FACS Analysis To investigate whether Aβ stimulation could result in CD40 protein expression on cultured HAEC, these cells were treated with $A\beta_{1-40}$, or $A\beta_{1-42}$ (5 μM) control peptide (5 μM) or IFN-γ (100 U/mL) for 48 hours after plating, and cell lysates were prepared for Western immunoblotting. As shown in FIGS. 2A–E, it was observed that CD40 expression in cultured HAEC treated with $A\beta_{1-40}$, or $A\beta_{1-42}$ or IFN-γ is greater than with control peptide or Aβ-free conditions (approximate 2-fold increase following Aβ treatment, and 2.5-fold increase with IFN-γ treatment). CD40 expression between control peptide-treated and Aβ-free AEC was relatively similar. To quantify CD40 cell-surface protein expression, flow cytometry was performed, and results also showed that $A\beta_{1-40}$, or $A\beta_{1-42}$ or IFN-γ significantly induce CD40 expression on cultured HAEC compared to control peptide or Aβ-free conditions (One-way ANOVA revealed significant between-groups differences, F(4,14)–123.49, p<0.001; post-hoc testing revealed significant differences between the Aβ-free condition or control peptide treatment and $A\beta_{1-40}$, or $A\beta_{1-42}$ or IFN-γ treatment, p<0.001 for each comparison), corroborating the Western immunoblotting data.

Previous reports have shown that overexpression of amyloid precursor protein or exogenous addition of Aβ peptides can have cytotoxic effects on cultured endothelial cells [15,20]. In order to determine if Aβ-induced endothelial CD40 expression was accompanied by cell injury, cytotoxicity was quantified by LDH release assay 48 hours after stimulation of HAEC with 500 nM $A\beta_{1-40}$, or $A\beta_{1-42}$ or control peptide. Results showed no significant induction of cell injury in HAEC for each of the treatments used over the time course examined (by One-way ANOVA, F(2,14)–0.040, p=0.961), suggesting that Aβ induction of CD40 is an early consequence of Aβ treatment which occurs prior to Aβ-induced cytotoxicity.

CD40 Expression on Cultured HAEC is Aβ Dose-dependent

Figure 4:
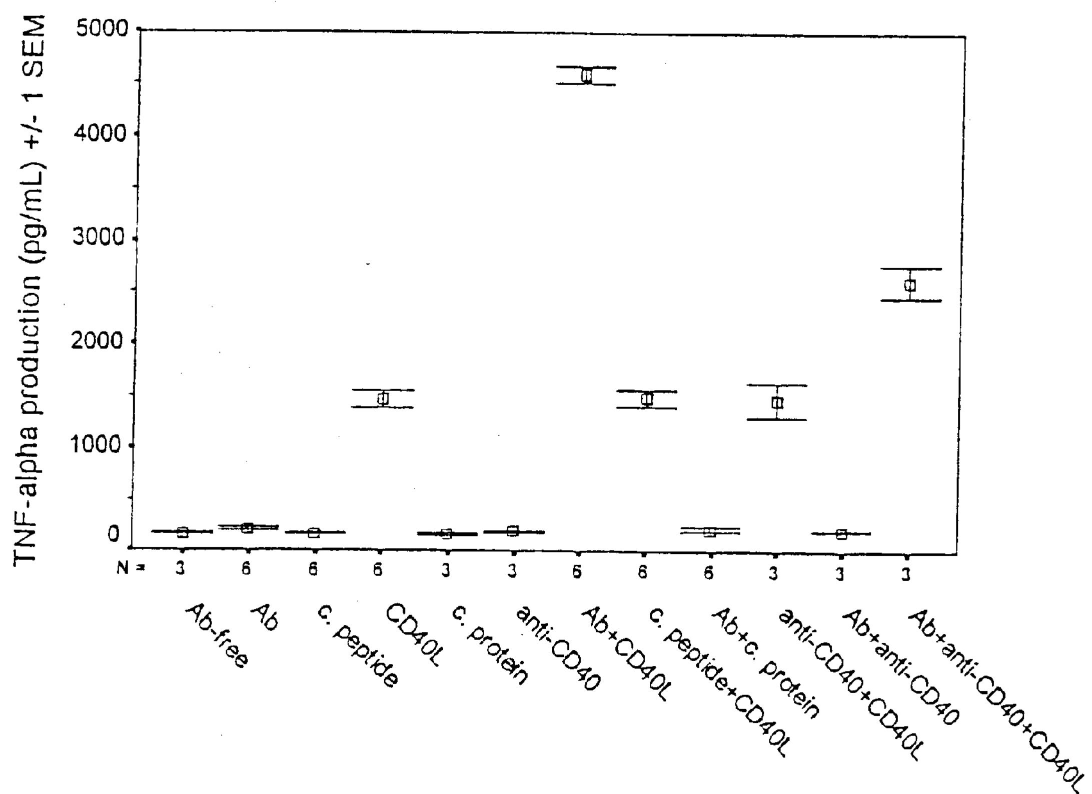
FIG. 4: is a graph that shows that ligation of Aβ-dependent CD40 reduces TNF-α microglial production; data shown represent mean values ±1 SEM of TNF-α production; numbers for each group are shown below the abscissa; ANOVA revealed significant main effects of A$\beta_{1-42}$ (p<0.001), CD40L (p<0.001), anti-CD40 antibody (p<0.001), but not for either control peptide (c. peptide) or control protein (c. protein); ANOVA also showed significant interactive terms between A$\beta_{1-42}$ and CD40L (p<0.001) and among A$\beta_{1-42}$, CD40L, and anti-CD40 antibody (p<0.001); post-hoc comparison between A$\beta_{1-42}$ and CD40L and the A$\beta_{1-42}$+CD40L +anti-CD40 experimental conditions revealed a significant difference (p<0.001), indicating partial blockade of TNF-α release by the anti-CD40 antibody.
Figure 5:
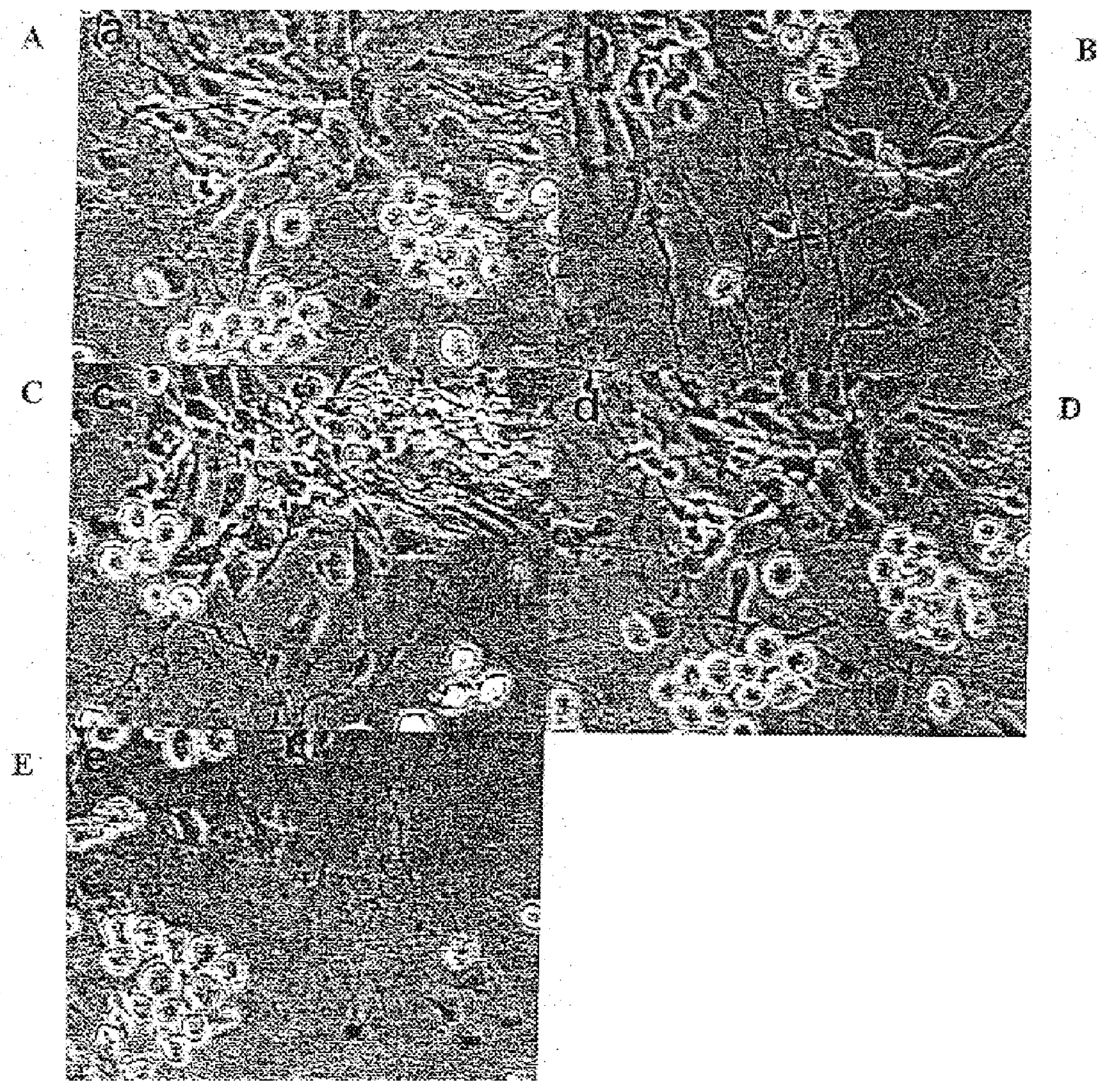
FIG. 5A: is a photomicrograph that shows there is no change in cortical neurons when cultured with microglia cells.
FIG. 5B: is a photomicrograph that shows there is no change in cortical neurons when incubated with A$\beta_{1-42}$ (250 nM) N9 microglia cells.
FIG. 5C: is a photomicrograph that shows there is no change in cortical neurons when incubated with N9 microglia cells co-treated with CD40L (0.5 μg/ml)
FIG. 5D: is a photomicrograph that shows there is no change in cortical neurons when incubated with N9 microglial are co-treated with control peptide (250 nM) and CD40L (0.5 μg/ml)
FIG. 5E: is a photomicrograph that shows there is no neuronal degeneration when N9 microglial are co-treated with A$\beta_{1-42}$ (250 nM) and CD40L (0.5 μg/ml)
Figure 6:
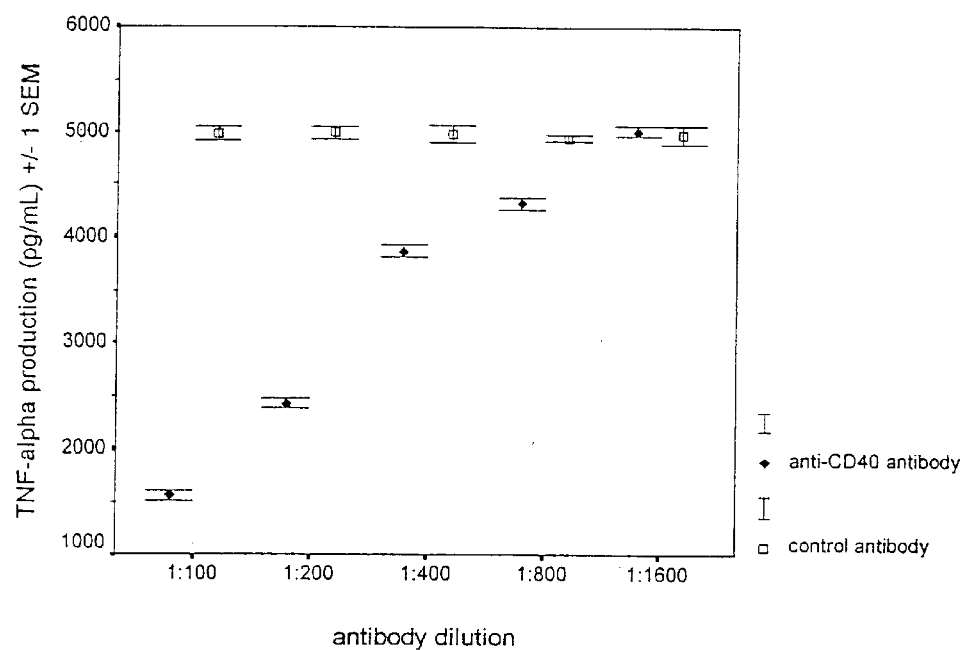
FIG. 6 shows that anti-CD40 antibody dose-dependently reduces the effect of ligation of CD40 on TNF-α production; data shown represent mean values ±1 SEM of TNF-α production; N=3 for each group; ANOVA showed main effects of antibody dilution (p<0.001) and anti-CD40 antibody (p<0.001), and a significant interaction between antibody dilution and anti-CD40 antibody ($p<0.001$), indicating an anti-CD40 antibody dilution-dependent increase in TNF-$\alpha$ production.

To determine if endothelial CD40 expression could be Aβ dose-dependent, HAEC treated with $A\beta_{1-40}$, or $A\beta_{1-42}$, control peptide, IFN-γ, or $A\beta_{1-40}$-treated HRCC (which do not express CD40) were examined using a CD40 expression assay [4,12]. As shown in FIG. 4, these data indicate that treatment with $A\beta_{1-40}$, or $A\beta_{1-42}$ results in a marked increase in endothelial CD40 which is dose-dependent compared to Aβ-treated HRCC or dose-matched control peptide-treated HAEC. ANOVA revealed significant treatment effects of $A\beta_{1-40}$ dose (F(4, 14)=78.10, p<0.001) and $A\beta_{1-42}$ dose (F(4, 14)=191.87, p<0.001) but not for control peptide dose (F(4, 14)=1.87, p=0.193) or HRCC subjected to $A\beta_{1-40}$ doses (F(4,14)=0.25, p=0.906). One-way ANOVA across doses revealed significant between-groups differences (F(3,59)= 45.09, p<0.001), and post-hoc testing showed significant differences between control peptide-treated HAEC and $A\beta_{40}$-treated HRCC (p<0.01), control peptide and $A\beta_{1-42}$ (p<0.001). Furthermore, IFN-γ-treatment of HAEC also results in dose-dependent induction of endothelial CD40 (FIG. 6), as evidenced by a significant treatment effect of IFN-γ dose (F(4, 14)=63.59, p<0.001) by One-way ANOVA.

Aβ-induced Endothelial CD40 is Functional

To investigate whether A-induced expression of endothelial CD40 could be functional, cultured HAEC were pretreated with 500 nM of either $A\beta_{1-40}$, or $A\beta_{1-42}$, control peptide (500 nM), IFN-γ (10 U/mL) or untreated (Aβ-free) for 48 hours. A second group of cells was subjected to these same treatments and incubated with CD40L (0.5 mg/mL) for eight hours following the initial 48 hour treatment period. IL-1β release was then quantified using a human IL-1β ELISA kit as described in materials and methods. No significant differences between treatment groups in the absence of CD40L stimulation (by one-way ANOVA, F(4, 14)=1.64, p=0.240) were observed, indicating that treatment with Aβ peptides or IFN-γ alone is not sufficient to elicit IL-1β $Aβ_{1-42}$ release. However, following CD40 ligation, significant differences were found between treatment groups in levels of human IL-1β production (by one-way ANOVA, $F(4,14)=206.12$, $p<0.001$), and post-hoc testing showed significant differences between control peptide and either $Aβ_{1-40}$ ($p<0.001$) or ($p<0.001$). Interestingly, there is noted the statistical interaction between CD40 ligation and $Aβ_{1-40}$ ($F(1,29)=302.00$, $p<0.001$), $Aβ_{1-42}$ showing that ligation of CD40 and treatment with either Aβ peptides or IFN-γ results in a synergistic effect. A low level of endogenous IL-1β release was detected in the CD40L and Aβ-free condition (approximately 50 pg/mg total protein), which was similar to the observed IL-1β release was detected in the CD40L and control peptide co-treatment condition, indicating that control peptide treatment does not alter CD40L-induced IL1β release.

DISCUSSION

The focus of the present invention on Aβ induction of CD40 in endothelial cells follows recent reports that Aβ peptides play a role in inflammation-mediated vascular endothelium dysfunction [14,32]. The above experimental data provides evidence that $Aβ_{1-40}$, or $Aβ_{1-42}$, like IFN-γ, dose-dependently induce expression of functional CD40, on cultured HAEC following 48 hour pre-treatment, suggesting that Aβ peptides participate in vascular endothelial dysfunction through CD40-mediated inflammation. This effect was observed with a relatively high concentration of Aβ, elevated levels of which are found co-localized with smooth muscle cells in cerebral amyloid angiopathy, which occurs in over 80% of AD patients [6].

In order to determine if ligation of endothelial CD40 could result in production of pro-inflammatory cytokines, IL-1β was measured following treatment with IFN-γ or Aβ peptides. Human IL-1β was significantly increased in cultured media of Aβ or IFN-γ-treated HAEC following CD40 ligation, showing that endothelial CD40 initiates vascular inflammation by promoting secretion of IL-1β. The effect of IFN-γ treatment on CD40 induction was more pronounced than Aβ's effect, suggesting either a dose-related phenomenon or that IFN-γ is more potent than Aβ in inducing CD40-mediated endothelial IL-1β. There was not observe a significant induction of endothelial cell death by LDH release assay between treatment groups during the time course examined by IL-1β release assay (by One-way ANOVA, $F(6,41)=0.322$, $p=0.921$), supporting the hypothesis that stimulation of the CD40 pathway in endothelial cells results in an early pro-inflammatory cascade which later promotes cell injury, rather than induce cytotoxicity acutely.

Example 3

Materials and Methods

Materials

Cell culture media, fetal bovine serum (FBS) and other culture reagents were supplied by Clonetics, GibcoBRL and Sigma. $Aβ_{1-40}$, $Aβ_{1-42}$ and $Aβ_{25-35}$ were supplied by RBI and/or M.D. Enterprise. All Aβ peptides used were freshly dissolved in Sigma $H_2O$ and aliquots were promptly stored at −20° C. The ABC-based enzyme-linked immunoassay (ELISA) kit was obtained from Sigma. The monoclonal antibodies (mAbs) against human CD40, CD45, CD40L, IFN-γR, IL-1β, IFN-γ ELISA kit was ordered from R&D Systems or Endogen, respectively.

Cell Cultures

Human aortic endothelial cell (HAEC, 3$^{rd}$ passage) line was obtained from Clonetics, and grown in endothelial cell growth medium (EGM, Clonetics) containing endothelial cell basal medium, supplemented with 10 ng/ml human recombinant epidermal growth factor, 1 μg/ml hydrocortisone, 12 μg/ml bovine brain extract, 2% FBS, 50 μg/ml Gentamicin and 50 ng/ml Amphotericin B. As described by the manufacturer, this HAEC line has tested positive for the presence of von Willebrand's factor, uptake of the reagent Dil-Ac-LDL and negative for smooth muscle α-actin. The manufacturer's instructions recommend use of these cells within 15 passages, the cells used in these experiments were between the fourth and seventh passage. The human aortic smooth muscle cell line (HASM, 18$^{th}$ passage) was purchased from ATCC, and grown in smooth muscle cell growth medium (SmGM-2, Clonetics) containing smooth muscle cell basal medium supplemented with 0.5 ng/ml human recombinant epidermal growth factor, 2 ng/ml human fibroblast growth factor, 5 μg/ml insulin, 5% FBS, 50 μg/ml Gentamicin and 50 ng/ml Amphotericin B. HASM cells were used between the 20$^{th}$ and 23$^{rd}$ passage in these experiments. All cells were maintained at 37° C. in an atmosphere containing 5% $CO_2$. HAEC and HASM cells were seeded for treatment in 96-well plates at $1\times10^4$ and $2\times10^4$ cells/well, respectively, one day after subculturing.

Cell-ELISA

In vitro measurement of Aβ-induced changes in expression of the inflammatory cell-surface molecules CD40 and IFN-βR in cultured HAEC and HASM cells was performed using a slightly modified ABC-based cell-ELISA (CELISA). Briefly, subcultured HAEC or HASM cells in flat-bottomed, 96-well tissue culture plates were exposed to the optimal concentration of $Aβ_{1-40}$, $Aβ_{1-42}$ and $Aβ_{25-35}$ for 48 hours and then incubated for 30 minutes at 4° C. with the primary antibodies (5 μg/ml, diluted in culture media) against the tested molecules. After PBS washes, 4% neutral formalin solution (Sigma) was used for fixation of the cells. Following quenching of the endogenous peroxidase activity with 3% $H_2O_2$ and routine blocking of non-specific binding, the biotinylated specific secondary antibodies against the primary antibodies (goat anti-mouse or anti-rabbit IgG) were applied. The combination of EXTRAVIDIN® Proxidase and the subsequent color reaction was performed strictly according to the manufacturer's instructions in the EXTRAVIDIN® Peroxidase Staining Kit (Sigma). The absorbance of 405 nm was then measured using a microplate reader (SPECTRAmax 250, Molecular Devices). The optical density (O.D.) value for the wells in the absence of the primary antibody for each group was considered as background and subtracted as the blank. In addition, stimulation with IFN-γ for CD40 was included as a positive control in the appropriate plate. Since CD45 is not expressed by endothelial or smooth muscle cells, the assays for expression of CD45 in these Aβ-treated cells were used as negative controls throughout the experiment. In addition, to evaluate the degree of cell death or proliferation in the Aβ-treated, cells, parallel experiments were performed using the MTS (3-(4, 5-dimethylthiazol-2-yl)-5-(3-carboxymethoxyphenyl)-2-(4-sulfophenyl)-2H-tetrazolium) cell-proliferation kit (Promega).

ELISAs for Cytokines

Human aortic endothelial cells were treated with increasing concentrations of either $Aβ_{1-40}$, or $Aβ_{1-42}$ for 24 hours, after which the culture media were collected and transferred to new 96-well plates. The assay for either IL-1β or IFN-γ was performed in strict accordance with the manufacturer's instructions for the respective assay kits.

Activation of CD40 Signalling

Activation of CD40 signalling can be achieved by stimulation with either CD40L or certain anti-CD40 mAbs [36]. Since synthetic CD40L is not commercially available, one of the anti-CD40 mAbs (clone 3/23), which has been reported to activate CD40 signalling [29], was used to mimic the effect of interaction of CD40–CD40L. All Aβ-treated cells were incubated with 1 μg/ml anti-CD40 mAb 93/23) for four hours followed by CELISA.

Western Blotting

Human aortic endothelial cells treated with vehicle $A\beta_{1-40}$, $A\beta_{1-42}$ or IFN-γ, either in the presence or absence of mAb (3/23) were lysed in cold lysis buffer containing 1 mM EDTA, 10 mM Tris/HCl (pH 7.4), 150 mM NaCl, 0.5% Nonidet P-40, 0.2 mM sodium orthovanadate, 1 mM EGTA (pH 8.0), 0.2 mM PMSF, and 1% Triton X-100. The total protein was estimated using the Bio-Rad protein assay. An aliquot corresponding to 100 μg of total protein of each sample was separated by SDS/PAGE (polyacrylamide gel electrophoresis) and transferred electrophoretically to PVDF filters. Non-specific binding of antibody was blocked with 5% non-fat dry milk, in 20 mM Tris/HCl, pH 7.5/150 mM NaCl/0.1% Triton X-100. Immunoblotting was carried out with the appropriate antibody followed by alkaline phosphatase-conjugated secondary anti-immunoglobulin antibodies. These were then developed by the chemiluminescence method (Bio-Rad).

Statistical Analysis

The results were expressed as mean±S.D. and analyzed by analysis of variance (ANOVA) using SPSS version 7.5. Post-hoc comparisons of means were made using Scheffe's, or Tukey's method where appropriate.

Results

Cell Toxicity and Proliferation Induced by Aβ

For all ELISAs and CELISAs, no significant proliferation was observed in either HAEC or HASM cells resulting from Aβ treatment. Also, Aβ did not induce significant cell death in HASM cells. However, a significant amount of cell death was observed in HAEC treated with either 10 or 20 μM of $A\beta_{1-40}$, $A\beta_{25-25}$measured by MTS assay. Corrections to the assays were not employed since this effect would only serve to increase the significance of the results reported.

Aβ Peptides Induce Secretion of IL-1β and IFN-γ from HAEC

In order to measure Aβ's ability to directly stimulate the endothelial cells to secrete IL-1β and IFN-γ, HAEC were treated with increasing concentrations of either $A\beta_{1-40}$ or $A\beta_{1-42}$ for 24 hours. The resulting cell culture media were assayed for IL-1β or IFN-γ using ELISA. As shown in FIGS. 1A–C, $A\beta_{1-42}$ increases the secretion of IL-1β and IFN-γ in a dose-dependent manner ($p<0.001$ by ANOVA). The lowest effective concentration was determined to be 100 nM for IFN-γ ($p<0.001$ by ANOVA). The lowest effective concentration was determined to be 100 nM for IFN-γ ($p<0.01$) and 1 μM for IL-1β ($p<0.01$). In contrast, $A\beta_{1-40}$ does not show a dose-dependent effect on the induction or secretion of either cytokine in the tested concentrations. However, the largest dose of $A\beta_{1-40}$ (20 μM) does induce a significant production of IFN-γ vs. control ($p<0.05$), and has no effect IL-1β secretion. These data suggest that $A\beta_{1-42}$ is capable of activating HAEC and increasing the secretion of cytokines. Furthermore, the activation of HAEC is more sensitive to $A\beta_{1-42}$ than $A\beta_{1-40}$.

Aβ Peptides Up-regulate the Expression of IFN-γR

The effects of Aβ peptides on the expression of IFN-γR was investigated in order to better understand the significance of Aβ-induced cytokine secretion. There is no expression of IFN-γR in normal HAEC, and neither $A\beta_{1-40}$ nor $A\beta_{25-35}$ modulate the IFN-γR expression. Only $A\beta_{1-40}$ induces a significant effect on IFN-γR ($p<0.05$) in HASM cells. These results suggest that Aβ not only increases the cytokine secretion, but also up-regulates receptor expression and that $A\beta_{1-42}$ preferentially activates endothelial cells rather than smooth muscle cells, while $A\beta_{1-42}$ has the opposite effect. Further confirmation of this effect was provided with Western blotting.

Aβ Peptides Induce the Expression of CD40 in a Dose-dependent Manner

To further characterize the inducibility of CD40 by Aβ, the dose effect of both $A\beta_{1-40}$ and $A\beta_{1-42}$ on CD40 expression in HAEC was explained. The results show that $A\beta_{1-40}$ and $A\beta_{1-42}$ dose-dependently increase CD40 expression in HAEC. The lowest effective concentrations were 100 nM of $A\beta_{1-42}$ ($p<0.001$) and 10 μM of $A\beta_{1-40}$, respectively. These data show that concentrations of $A\beta_{1-42}$ in the nanomolar range can still induce a significant increase of CD40 expression in HAEC and that the differential effects of Aβ types are consistent with those of the previous observations.

IL-1β and IFN-γ Increase the Expression of CD40 and IFN-γR

The results show the effects of cytokines on the expression of CD40 and IFN-γR. Both IL-1β and IFN-γ significantly ($p<0.001$) up-regulate the expression of CD40 and IFN-γR. This conclusion is confirmed, since the mAbs against either IL-1β or IFN-γ significantly reduce the $A\beta_{1-42}$ up-regulated expression of CD40 ($p<0.001$) and IFN-γR ($p<0.01$) in HAEC.

Activation of CD40 Signalling Further Increases the Aβ-induced Effects

To further investigate the possible interactions between the Aβ-induced changes in cytokine release and CD40 expression, mAp (3/23) was used against human CD40 to mimic the activation of CD40 signalling and to observe the effect of CD40 signalling on the Aβ-induced IFN-γ secretion and IFN-γR expression. The ligation of CD40 further increases the Aβ-induced IFN-γ secretion and IFN-γR expression. For Aβ-induced IFN-γR expression in HAEC, only $A\beta_{1-42}$ displayed a significant effect ($p<0.001$), as well as a significant interaction with the mAb ($p<0.001$). Western blotting for Aβ-induced IFN-γR expression after treatment with mAb (3/23) confirms the enhancement of this effect by ligation of CD40. These results suggest that the activation of CD40 signalling amplifies the Aβ-induced effects via common signal transduction pathway. Ligation of CD40 by mAb (3/23) further increases IFN-γR expression in HASM cells in a additive way for $A\beta_{1-42}$ and $A\beta_{25-35}$, and in a synergistic way for $A\beta_{1-40}$ (interactive term, $p<0.001$ by ANOVA).

Aβ directly induces both CD40 expression, and the secretion of IL-1β and IFN-γR in either endothelial or smooth muscle cells can also be directly induced by specific types of Aγ. These data suggest that although cytokines such as IL-1β and IFN-γ can be mainly produced by recruited circulating T-cells and macrophages, Aβ can activate vascular cells and stimulate the production of functional cytokines. Moreover, using either recombinant human cytokines or neutralization mAbs against the cytokines, it is shown that both IL-1β and IFN-γ can up-regulate the expression of both CD40 and IFN-γR. These data show that different cytokines can synergistically modulate the expression of multiple genes including their own and those of their receptors [20, 30]. Furthermore, these results show that Aβ-induced cytokine production can amplify the Aβ effects by auto-regulation or further increase in CD40 expression. This experiment shows that the activation of CD40 signalling further increases production of all the tested molecules. Also infiltration of T-cells/macrophages into the vasculature, which is mediated by the increased expression of adhesion molecules observed in previous studies, would result in a further increase in cytokine production. Collectively, these results show that Aβ can function as an inflammatory stimulator to activate vascular cells and is responsible for an auto-amplified inflammatory molecular cascade, specifically mediated by interactions among adhesion molecules, CD40–CD40L and cytokines.

AS dose-dependently increases expression of CD40 and cytokine secretion in HAEC. The effective concentration of Aβ, which induces both cytokine secretion and CD40 expression, starts in the nanomolar range, a much lower concentration than that required to induce direct cytotoxicity (10 to 100 μM [35]). It is also evident that for a given cell type, the induction of an inflammatory cascade is dependent upon the type of Aβ peptide. Both physiologically produced Aβ peptides ($A\beta_{1-40}$ and $A\beta_{1-42}$), are able to induce inflammatory responses, with $A\beta_{1-42}$ inducing much stronger effects in endothelial cells than in smooth muscle cells. By contrast $A\beta_{1-40}$ is a more potent stimulator of smooth muscle cells than endothelial cells. These results show that in vivo, $A\beta_{1-42}$ mainly activates the vascular endothelial cells which contributes to disruption of blood-brain barrier in CAA and AD. Furthermore, the presence of $A\beta_{1-40}$, which is the predominant vascular isoform of Aβ in CAA and AD, contributes to the development of inflammatory processes in the smooth muscle layer and result in smooth muscle degeneration in these diseases.

Aβ-induced inflammatory cascades can result in the following changes:

(1) Increased expression of adhesion molecules in vascular cells, which is the mechanism of infiltration of T-cells and macrophages in the cerebrovasculature in CAA[42].

(2) Enhanced CD40–CD40L interactions, which not only cause a further increase in the expression of adhesion molecules and the secretion of cytokines, but also strengthen the antigen-presenting capacity and increase secretion of metalloproteinases such as MMP1, MMP2, MMP3 and MMP9 [[23,32], see Refs. [15, 19,27] for reviews]. This increase in matalloproteinases is responsible for the disruption of the blood-brain barrier in the late stages of CAA.

(3) Increased production of cytokines, which influences various processes in CAA pathogenesis other than only inflammation [see Ref. [20] for review]. For examples, see the following.

(a) Either IL-1β, IFN-γ or tumor necrosis factor-α can individually or synergistically induce smooth muscle degeneration by apoptosis [9, 11, 12].

(b) The stimulation of nitric oxide synthase by cytokines could either influence the vasomotor tone or induce toxic effects on neighboring cells [10].

(c) IL-1 and transforming growth factor-β increase the production of endothelins [21] which results in increased vasotension and reduced cerebral blood flow.

(d) IL-1 up-regulated the expression of Aβ precursor protein in vascular cells, an event associated with the abnormal accumulation of Aβ in the cerebrovasculature [8,14], which in turn enhances the Aβ-induced inflammatory cascades.

(e) Cytokines are known to modulate endothelial functions that govern the formation and stability of blood thrombi [20] and therefore contributes to cerebral hemorrhage in CAA.

(f) Cytokines can also increase the permeability of the blood-brain barrier and increase their own production, or the production of other cytokines within brain parenchyma [3,28,31], which suggests that the peripheral cytokines can also play a significant role in pathogenesis of CAA. Overall, the increased production of cytokines can be the major outcome of Aβ-induced inflammatory cascades and contribute to diverse processes at different stages of CAA and AD.

Since the CD40–CD40L interaction is the primary regulatory event in Aβ-induced inflammatory cascades, blocking this interaction provides a therapeutic strategy. Therefore, blockage of the CD40–CD40L interaction of neutralization of the effects of IL1β and IFN-γ are then immediately implicated as therapeutic targets for CAA and AD.

Throughout this application, various publications, including U.S. patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. L. Meda et al., *Nature* 374, 647 (1995).
2. C. K. Combs, D. E. Johnson, S. B. Cannady, T. M. Lehman and G. E. Landreth, *J. Neurosci.* 19, 928 (1999); R. N. Kalaria, *Curr. Opin. Hematol.* 6, 15 (1999).
3. U. Schonbeck et al., *J. Biol. Chem.* 272, 19569 (1997); G. D. Sempowski, P. R. Chess and R. P. Phipps, *J. Immunol.* 158, 4670 (1997); K. Karmann, C. C. Hughes, J. Schechner, W. C. Fanslow and J. S. Pober, *Proc. Natl. Acad. Sci. USA* 92, 4342 (1995).
4. See (36) for microglial culture methods and characterization.
5. See (36) for reagents and suppliers.
6. See (36) for microglial treatment conditions and RT-PCR methods.
7. See (36) for microglial western blot methods.

8. See (36) for microglial FACS analysis.
9. All analyses were performed using SPSS for windows release 7.5.1. Data were analyzed using analysis of variance (ANOVA) followed by post-hoc comparisons of means where appropriate using Bonferonni's method. Single mean comparisons were performed using t test for independent samples. Alpha levels were set at 0.05 for each analysis.
10. Web FIG. 1 can be found at www.sciencemag.org/feature/data/1. Tg $APP_{sw}$ mice are 2576 line crossed with C57B6/SJL as described in K. K. Hsiao et al., *Science* 274, 99 (1996); K. K. Hsiao et al., *Neuron* 15, 1203 (1995). To further characterize adult mice, we analyzed CD40 and TNF-α protein expression by Western immunoblot (densitometric signal ratio to actin) in brain lysates from 12-month old Tg $APP_{sw}$ or control littermates. CD40 and TNF-α protein levels were significantly ($p<0.01$) increased in Tg $APP_{sw}$ mice compared to control littermates (CD40, mean=1.01±0.03 SEM vs. 0.75±0.03; TNF-α, 1.04±0.01 vs. 0.81±0.04).
11. See (36) for primary culture microglia isolation, culture and characterization.
12. Soluble $Ab_{1-40}$ was quantified in the culture media of Tg $APP_{sw}$ or control littermate-derived microglia 48 h after plating using the Ab40 ELISA kit (QCB, Hopkinton, Mass.), in strict accordance with the manufacturer's instruction. Data showed a significant ($p<0.001$) increase in soluble $Ab_{1-40}$ levels from Tg $APP_{sw}$ microglia (mean=291.90±21.81 SEM pg/mg total cellular protein) compared to control littermate-derived microglia (23.41±7.75).
13. Web FIG. 2 can be found at www.sciencemag.org/feature/data/1.
14. See (36) for details of microglial co-stimulation with Aβ and cytokines.

15. G. Ruggiero et al., *J. Immunol*. 156, 3737 (1996); D. Hollenbaug et al., *J. Exp. Med*. 182, 33 (1995); R. W. Denfeld etal., *Eur. J. Immunol*. 26, 2329 (1996).

16. Web FIG. 3 can be found at www.sciencemag.org/feature/data/1.

17. M. Huberman et al., *J. Neuroimmunol*. 52,147 (1994).
18. A. Klegeris, D. G. Walker and P. L. McGeer, *Brain Res*. 747, 114 (1997).
19. G. M. Castillo, C. Ngo, J. Cummings, T. N. Wight and A. D. Snow, *J. Neurochem* 69, 2452 (1997).

20. See (36) for microglial treatment conditions and TNF-α ELISA and RT-PCR methods.
21. Web FIG. 4 can be found at www.sciencemag.org/feature/data/1.
22. See (36) for details of conditions, treatment and immunochemistry for co-culture experiments.
23. See (36) for details of neuronal and co-culture $^{51}Cr$ release and LDH assay.

24. J. Tan, et al., J. Neuroimmunol. 97, 77 (1999).
25. J. Xu, et al., *Immunity* 1, 423 (1994).

26. See (36) for details of transgenic microglial TNF-α release and verification of CD40L deficiency.

27. A. Schneider, J. Biernat, M. von Bergen, E. Mandelkow and E. M. Mandelkow, *Biochemistry* 38, 3549 (1999); C. Sturchler-Pierrat, et al., *Proc. Natl. Acad. Sci. USA* 94,13287 (1997); N. D. James, et al., *Neurobiol. Aging* 17, 235 (1996); L. S. Higgins, J. M. Rodems, R. Catalano, D. Quon and B. Cordell, *Proc. Natl. Acad. Sci. USA* 92, 4402 (1995); I. Genis, A. Fisher and D. M. Michaelson, *J. Neurochem*. 72, 206 (1999).

28. See (36) for details of phospho-tau analysis.

29. T. Uchihara, H. Akiyama, H. Kondo and K. Ikeda, Stroke 28,1948 (1997).
30. F. Mach, et al., *Proc. Natl. Acad. Sci. USA* 94, 1931 (1997).
31. Ellis, R. J. et al., *Neurology* 46, 1592 (1996).
32. V. H. Oleana, A. Salehi and D. F. Swaab, *Neuroreport* 9, 1451 (1998); J. Rogers, J. Luber-Narod, S. D. Styren and W. H. Civin, *Neurobiol. Aging* 9, 339 (1988).
33. V. Henn et al., *Nature* 391, 591 (1998).
34. Q. X. Li etal., *Blood* 84, 133 (1994).

35. Supplemental material is available at the Science Web site (www.sciencemag.org/feature/data/1)

36. Dr. Paola Ricciardi-Castagnoli for provided the murine microglial cell lines (N9) and Dr. Jean-Yves Bonnefoy for provided the human CD40L. Dr. Hua Yu assisted in the $^{51}Cr$ release assay and Andon Placzek assisted in mice genotyping.

What is claimed is:

1. An in vitro assay method for determining the effect of an agent on Alzheimer's disease pathology comprising the steps of:

a. treating microglial cells with Aβ peptides;

b. adding CD40 ligand (CD40L) to the microglial cells;

c. adding a therapeutic agent to the microglial cells;

d. measuring Alzheimer's disease pathology in vitro; and e. correlating the disease pathology to the effect of an agent on Alzheimer's disease.

2. The method according to claim 1, wherein said adding a therapeutic agent step is further defined by the therapeutic agent being an antibody.

3. The method according to claim 1, wherein said measuring step further includes measuring Alzheimer's disease pathology by microglial activation, increased phosphorylation of tau protein, formation of neurofibrillary tangles, or neuronal cell injury.

4. The method according to claim 3, wherein said measuring step is further defined by determining microglial activation by TNF-α production or nitric oxide release or inducible nitric oxide synthase production or glutamate production.

5. The method according to claim 3, wherein said measuring step is further defined by determining Alzheimer's disease pathology by the degree of tau protein phosphorylation.

6. The method according to claim 1, wherein said measuring step is further defined by determining Alzheimer's disease pathology by modulation of Aβ deposition in vitro.

7. The method according to claim 3, wherein said measuring step is further defined by determining neuronal cell injury by a method selected from the group consisting essentially of LDH release, Chromium-51 release, and microscopy.

8. A method of determining therapeutic effectiveness of an agent for Alzheimer's disease comprising the step of measuring in vitro the inhibition of the CD40–CD40L binding in the presence of the agent and correlating any increase in inhibition of CD40–CD40L binding to an increase in effectiveness of the agent for Alzheimer's disease, followed by measuring the agent's effectiveness in reducing Alzheimer's disease pathology.

9. The method according to claim 8, wherein said measuring step is further defined by the agent being an antibody.

10. An in vitro assay kit for determining the effect of an agent on Alzheimer's disease pathology comprising:

Aβ peptides for adding to microglial cells;

CD40 ligand for adding to the microglial cells;

a therapeutic agent for adding to the microglial cells; and measuring means for quantifying Alzheimer's disease pathology in vitro.

11. The assay according to claim 10, wherein said therapeutic agent is an antibody.

12. The assay according to claim 10, wherein said measuring means measures microglial activation, increased phosphorylation of tau protein, formation of neurofibrillary tangles, and neuronal cell injury.

* * * * *

UNITED STATES PATENT AND TRADEMARK OFFICE

CERTIFICATE OF CORRECTION

PATENT NO. : 6,787,318 B1
DATED : September 7, 2005
INVENTOR(S) : Tan et al.

It is certified that error appears in the above-identified patent and that said Letters Patent is hereby corrected as shown below:

Title page,
Item [56], References Cited, OTHER PUBLICATIONS, "Borreback," reference, "Borreback" should read -- Borrebaeck --
Item [57], ABSTRACT,
Line 13, "device for reassuring" should read -- device for measuring --

Column 17,
Line 45, "oligbnucleotides" should read -- oligonucleotides --
Line 51, after "fragment [23].", insert the following:
-- PCR products were resolved on 1.2% ethidium bromide-stained agarose gels, and visualized by UV transillumination. Densitometric analysis was performed for cDNA bands using the Fluor-S™ Multimager with Quantity One™ software (Bio-Rad, CA) --

Column 22,
Line 32, "IFN-$\beta$R in cultured" should read -- IFN-$\gamma$R in cultured --

Signed and Sealed this

Twenty-first Day of June, 2005

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 21
<212> TYPE: DNA
<213> ORGANISM: artificial sequence
<220> FEATURE:
<221> NAME/KEY: artificial sequence
<222> LOCATION: (1)..(21)
<223> OTHER INFORMATION: primer

<400> SEQUENCE: 1

cctggcctca cctcgccatg g                                          21


<210> SEQ ID NO 2
<211> LENGTH: 21
<212> TYPE: DNA
<213> ORGANISM: artificial sequence
<220> FEATURE:
<221> NAME/KEY: artificial sequence
<222> LOCATION: (1)..(21)
<223> OTHER INFORMATION: primer
```

-continued

```
<400> SEQUENCE: 2

gaggggctcg cactgactgg g                                              21


<210> SEQ ID NO 3
<211> LENGTH: 20
<212> TYPE: DNA
<213> ORGANISM: artificial sequence
<220> FEATURE:
<221> NAME/KEY: artificial sequence
<222> LOCATION: (1)..(20)
<223> OTHER INFORMATION: primer

<400> SEQUENCE: 3

cagaggctcc cctaaatccc                                                20


<210> SEQ ID NO 4
<211> LENGTH: 20
<212> TYPE: DNA
<213> ORGANISM: artificial sequence
<220> FEATURE:
<221> NAME/KEY: artificial sequence
<222> LOCATION: (1)..(20)
<223> OTHER INFORMATION: primer

<400> SEQUENCE: 4

cacactgagt acttgcgctc                                                20
```